(12) United States Patent
Grandy et al.

(10) Patent No.: US 6,406,866 B1
(45) Date of Patent: *Jun. 18, 2002

(54) METHOD OF SCREENING OF A COMPOUND FOR BINDING TO MSOR

(75) Inventors: David K. Grandy; James R. Bunzow, both of Portland, OR (US); Olivier Civelli, Irvine, CA (US); Rainer Klaus Reinscheid, Irvine, CA (US); Hans-Peter Nothacker, Irvine, CA (US); Frederick James Monsma, Summit, NJ (US)

(73) Assignee: Oregon Health Sciences University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/048,916

(22) Filed: Mar. 26, 1998

Related U.S. Application Data

(60) Division of application No. 08/514,451, filed on Aug. 11, 1995, now Pat. No. 5,837,809, which is a continuation-in-part of application No. 08/149,093, filed on Nov. 8, 1993, now Pat. No. 5,658,783.

(51) Int. Cl.[7] .................. G01N 33/53; G01N 33/567; A61K 38/00; C07K 14/00; C12P 21/06

(52) U.S. Cl. .................. 435/7.2; 530/300; 530/350; 435/69.1

(58) Field of Search ................ 435/7.21, 7.2, 435/69.1; 530/350, 300

(56) References Cited

U.S. PATENT DOCUMENTS

| | | |
|---|---|---|
| 5,512,578 A | 4/1996 | Crain et al. |
| 5,658,783 A | 8/1997 | Grandy et al. ............... 435/325 |

FOREIGN PATENT DOCUMENTS

| | | |
|---|---|---|
| WO | WO 95/19986 | 7/1995 |

OTHER PUBLICATIONS

George DG et. al. "Current Methods in Sequence Comparison and Analepes" in Schlesinger, D.H. Macromolecular Sequenary and Synthesis–Selected Methods and Applications (New York, Alank. Liss Inc) pp. 127–149, 1988.*

Cunningham BC and Weils J.A; HgH Resolution Epitope Mapping of High Receptor Interactions by Alanine–Scanning Mutagenesis Source vol. 204, pp. 1081–1085, 1989.*

Brownstein, M.J., A Brief History of Opiates, Opioid Peptides, and Opioid Receptors, Proc. Natl. Acad. Sci. USA 90:5391–5393 (1993).

Bunzow et al., Molecular Cloning and Tissue Distribution of a Putative Member of the Rat Opioid Receptor Gene Family that is not a μ, δ, or k opioid receptor type, FEBS Letters 347:284–288 (1994).

Bzdega et al., Regional Expression and Chromosomal Localization of the δ Opiate Receptor Gene, Proc. Natl. Acad. Sci. USA 90: 9305–9309 (1993).

Chen et al., Molecular Cloning and Functional Expression of a μ–Opioid Receptor from Rat Brain, *Molecular Pharmacology* 44:8–12 (1993).

Chen et al., Molecular Cloning, Tissue Distribution, and Chromosomal Localization of a Novel Member of the Opioid Receptor Gene Family, FEBS Letters 347:279–283 (1994).

Di Chiara, G. and North, R.A., Neurobiology of Opiate Abuse, *TiPS* 13:185–193 (1992).

Evans et al., Cloning of a Delta Opioid Receptor by Functional Expression, *Science* 285:1952–1955 (1992).

Fakuda et al., Primary Structures and Expression from cDNAs of Rat Opioid Receptor δ–and μ–subtypes, FEBS Letters 327:311–314 (1993).

Goldstein, A., Binding Selectivity Profiles for Ligands of Multple Receptor Types: Focus on Opioid receptors, *TIPS* 8:456–459 (1987).

Kieffer et al., The δ–Opioid Receptor: Isolation of a cDNA by Expression Cloning and Pharmacological Characterization, *Proc. Natl. Acad. Sci.* USA 89:12048–12052 (1992).

Kristensen et al., The $Mu_1$, $Mu_2$, Delta, Kappa Opioid Receptor Binding Profiles of Methadone Stereoisomers and Morphine, *Life Sciences* 56:45–50 (1995).

Maneckjee, R. and Minna J.D., Nonconventional Opioid Binding Sites Mediate Growth Inhibitory Effects of Methadone on Human Lung Cancer Cells, *Proc. Natl. Acad. Sci.* USA 89:1169–1173 (1992).

McKnight and Rees, *Neurotransmissions* 7:1–6 (1991).

Meunier et al., Isolation and Structure of the Endogenous Agonist of Opioid Receptor–like $ORL_1$ Receptor, *Nature* 377:532–535 (1995).

Reinsheid et al., Orphanin FQ: A Neuropeptide That Activates an Opioidlike G Protein–Coupled Receptor, *Science* 270:792–794 (1995).

(List continued on next page.)

Primary Examiner—Gary L. Kunz
Assistant Examiner—Robert S. Landsman
(74) Attorney, Agent, or Firm—Klarquist Sparkman, LLP

(57) ABSTRACT

The present invention relates to a novel mammalian opioid receptor protein and ligands that bind to such proteins. The invention is directed toward the isolation, characterization and pharmacological use of an endogenous ligand that specifically binds to a novel mammalian opioid receptor protein heterologously expressed in mammalian cells. The invention specifically provides the isolated peptide ligand and analogues, derivatives and variants thereof. The invention specifically provides tyrosine substitution variants of the peptide ligand that specifically bind to the opioid receptor and can be radioiodinated. Also provided are methods of making such peptide ligands and methods of using the ligands for diagnostic and therapeutic uses and for the identification of other naturally-occurring or synthetic opioid receptor ligands.

12 Claims, 11 Drawing Sheets

OTHER PUBLICATIONS

Reinsheid et al., Structure–Activity Relationship Studies on the Novel Neuropeptide Orphanin FQ, *The Journal of Biological Chemistry* 271:14163–14168 (1996).

Saito et al., N23K, A Gene Transiently Up–Regulated During Neural Differentiation, Encodes a Precursor Protein for a Newly Identified Neuropeptide Nociceptin, *Biochemical and Biophysical Research Communications* 217:539–545 (1995).

Wang et al., μ Opiate Receptor: cDNA Cloning and Expression, *Proc. Natl. Acad. Sci. USA* 90:10230–10234 (1993).

Yasuda et al., Cloning and Functional Comparison of k and δ Opioid Receptors from Mouse Brain, *Proc. Natl. Acad. Sci. USA* 90:6736–6740 (1993).

Zagon et al., Localization of Methadone in the Brain of Young Rats by Computer–Assisted Autoradiography, *Neuroscience Research* 3:1–19 (1985).

Mollereau et al., "ORL 1, a novel member of the opioid receptor family. Cloning, functional expression and localization," FEBS Letters 341, 33–38, 1994.

* cited by examiner

```
CCGAGGAGCCATTCCCAGCCGCAGCAGACCCCAATCTAGAGTGAGAGTCATTGCTCAGTCCACTGCTCC        71
TGCCTGCCCGCCTTTCTGCTAAGCATTGGGGTCTATTTGCGCCCAGCTTCTGAAGAGGCTGTGTGCCG       142
TTGGAGAACTGTACTGAGTGGCTTGCAGGTGACAGCATGGAGTCCCTCTTTCCTGCTCCATACTGGGAG      214
                       M  E  S  L  F  P  A  P  Y  W  E
GTCTTGTATGGCAGCCACTTTCAAGGGAACCTGTCCCTCCTAAATGAGACCGTACCCCACCACCTGCTCCTC   286
 V  L  Y  G  S  H  F  Q  G  N  L  S  L  L  N  E  T  V  P  H  H  L  L  L
                                 ▲                  ▲
AATGCTAGTCACAGCGCCTTCCTGCCCCTTGGACTCAAGGTCACCATCGTGGGGCTCTACTTGGCTGTGTGC   358
 N  A  S  H  S  A  F  L  P  L  G  L  K  V  T  I  V  G  L  Y  L  A  V  C
                            ▲                 I
ATCGGGGGCTCCTGGGAACTGCCTCGTCATGTATGTCATCCTCAGGCACACCAAGATGAAGACAGCTACC    430
 I  G  G  L  L  G  N  C  L  V  M  Y  V  I  L  R  H  T  K  M  K  T  A  T
                    II
AACATTTACATATTTAATCTGGCACTGGCTGATACTGTGCTTGCTAACACTGCCCTTCCAGGGCACAGAC    502
 N  I  Y  I  F  N  L  A  L  A  D  T  L  V  L  T  L  P  F  Q  G  T  D
ATCCTACTGGGCTTCTGGCCATTTGGGAATGCACTCTGCAAGACTGTCATTGCTATCGACTACTACAACATG  574
 I  L  L  G  F  W  P  F  G  N  A  L  C  K  T  V  I  A  I  D  Y  Y  N  M
                                      III
TTTACCAGCACTTTTACTCTGACGGCCATGAGCGTAGACCGCTATGTGGCCATCTGCCACCCTATCCGTGCC  646
 F  T  S  T  F  T  L  T  A  M  S  V  D  R  Y  V  A  I  C  H  P  I  R  A
CTTGATGTTCGGACATCCAGCAAAGCCCAGGCTGTTAATGTGGCCATATGGGCCCTGGCTTCAGTGGTTGGT  718
 L  D  V  R  T  S  S  K  A  Q  A  V  N  V  A  I  W  A  L  A  S  V  V  G
                          *                    IV
```

FIG. 1A

```
GTTCCTGTTGCCATCATGGGGTTCAGCACAAGTGGAAGAGATGAAGAGATCGAGTGCCTGGTGGAGATCCCTGCC     790
 V  P  V  A  I  M  G  S  A  Q  V  E  D  E  E  I  E  C  L  V  E  I  P  A

CCTCAGGACTATTGGGGCCCTGTATTCGCAGCCCTCATCTGCATCTTCCTTCTCATCATCCCTGTGCTGATC     862
 P  Q  D  Y  W  G  P  V  F  A  I  C  I  F  L  F  S  F  I  I  P  V  L  I
                                          V

ATCTCTGTCTGCTACAGCCTCATGATTCGACGATTCGTGGTGTCCGTGTCTGCTTCAGGCGTCCGGGAGAAG     934
 I  S  V  C  Y  S  L  M  I  R  R  L  R  G  V  R  L  L  S  G  S  R  E  K

GACCGAAACCTGCGGCGTATCACTCGACTGGTGCTGGTAGTGGTGGCTGTGTTTGTGGGCTGTTGGACGCCT    1006
 D  R  N  L  R  R  I  T  R  L  V  L  V  V  V  A  V  F  V  G  C  W  T  P
                               VI

GTGCAGGTGTTTGTCCTGGTTCAAGGACTGGGTGTTCAGCCAGGTAGTGAGACTGCAGTGGCCATCCTGCGC    1078
 V  Q  V  F  V  L  V  Q  G  L  G  V  Q  P  G  S  E  T  A  V  A  I  L  R

TTCTGCACAGCCCTGGGCTATGTCAACAGTTGTCTCAATCCCATTCTCTATGCTTTCCTGGATGAGAACTTC    1150
 F  C  T  A  L  G  Y  V  N  S  C  L  N  P  I  L  Y  A  F  L  D  E  N  F
          VII

AAGGCCTGCTTTAGAAAGTTCTGCTGTGCTTCATCCCTGCACCGGGAGATGCAGGTTTCTGATCGTGTGCGG    1222
 K  A  C  F  R  K  F  C  C  A  S  S  L  H  R  E  M  Q  V  S  D  R  V  R

GCGATTGCCAAGGATGTTGGCCTTGGTTGCAAGACTTCTGAGACAGTACCACGGCCAGACTAGGCGTG        1294
 S  I  A  K  D  V  G  L  G  C  K  T  S  E  T  V  P  R  P  A
                                                            *

GACCTGCCCATGGTGCCTGTCAGCACCCATCCTACACCCAACACGGAGCTCACACAGGTCACTGC           1366
TCTCTAGGTTGACCCTGAACCTTGAGCATCTTGAGCCTTTTCTTTTTGGATCAGGATGTCAGT            1438
CCTAGAGGAAGACC
```

FIG. 1B

Amino acid alignment

```
LC132                                                    MESLFPAPYWEVL
Rat μ-Opioid Receptor        MDSSTGPGNTSDCSDPLAQASCSPAPGSWLNLS
Mouse δ-Opioid Receptor                         MELVPSARAELQSS
Mouse κ-Opioid Receptor          MESPIQIFRGDPGPTCSPSACLLP
```

I
```
LC132  YGSHFQGNLSLLNETVPHHLLLNASHSAFLPLGLKVTIVGLYLAVCIGGLLGNCL
μ-OR   HVDGNQSDPCGLNRTGLGGNDSLCPQTGSPSMVTAITIMALYSIVCVVGLFGNFL
δ-OR   PLVNLSDAFPSAFPSAGANASGSPGARSASSLALAIAITALYSAVCAVGLLGNVL
κ-OR   NSSSWFPNWAESDSNGSVGSEDQQLESAHISPAIPVIITAVYSVFVVGLVGNSL
```

II
```
LC132  VMYVILRHTKMKTATNIYIFNLALADTLVLLTLPFQGTDILLGFWPFGNALCKTV
μ-OR   VMYVIVRYTKMKTATNIYIFNLALADALATSTLPFQSVNYLMGTWPFGTILCKIV
δ-OR   VMFGIVRYTKLKTATNIYIFNLALADALATSTLPFQSAKYLMETWPFGELLCKAV
κ-OR   VMFVIIRYTKMKTATNIYIFNLALADALVTTTMPFQSAVYLMNSWPFGDVLCKIV
```

IV
```
LC132  IAIDYYNMFTSTFFTLTAMSVDRYVAICHPIRALDVRTSSKAQAVNVAIWALASVV
μ-OR   ISIDYYNMFTSIFTLCTMSVDRYIAVCHPVKALDFRTPRNAKIVNVCNWILSSAI
δ-OR   LSIDYYNMFTSIFTLTMMSVDRYIAVCHPVKALDFRTPAKAKLINICIWVLASGV
κ-OR   ISIDYYNMFTSIFTLTMMSVDRYIAVCHPVKALDFRTPLKAKIINICIWLLASSV
```

FIG. 2A

```
                                                                               V
LC132  GVPVAIMGSAQ  VEDEEIECLVEIPAP  QDYWGPVFAICIFLFSFIIPVLIISV
μ-OR   GLPVMFMATTK  YRQGSIDCTLTFSHP  TWYWENLLKICVFIFAFIMPILIITV
δ-OR   GVPIMVMAVTQ  PRDFAVVCMLQFPSP  SWYWDTVTKICVFLFAFVVPILIITV
κ-OR   GISAIVLGGTKVREDVDVIECSLQFPDDEYSWWDLFMKICVFVFAFVIPVLIIIV

VI
LC132  CYSLMIRRLRGVRLLSGSREKDRNLRRITRLVLVLVVVAVFVGCWTPVQVFVLVQGL
μ-OR   CYGLMILRLKSVRMLSGSKEKDRNLRRITRMVLVVVAVFIVCWTPIHIYVIIKAL
δ-OR   CYGLMLLRLRSVRLLSGSKEKDRSLRRITRMVLVVVGAFVVCWAPIHIFVIWTL
κ-OR   CYTLMILRLKSVRLLSGSREKDRNLRRITKLVLVVVAVFIICWTPIHIFILVEAL

VII
LC132  GVQPGSETAVAIL  RFCTALGYVNSCLNPILYAFLDENFKACFRKFCCASSLHRE
μ-OR                  ITIPETTFQTVSW  HFCIALGYTNSCLNPVLYAFLDENFKRCFREFCIPTSSTIE
δ-OR                  VDINRRDPLVVAALHLCIALGYANSSLNPVLYAFLDENFKRCFRQLCRTPCGRQE
κ-OR                  GSTSHSTAALSSY  YFCIALGYTNSSLNPVLYAFLDENFKRCFRDFCFPIKMRME

LC132  MQVSDRVRSIAKDVGLGCKTSETVPRPA 367
μ-OR   QQNSTRVRQNTREHPSTANTVDRTNHQLENLEAETAPLP 398
δ-OR   PGSLRRPRQATTRERVTACTPSDGPGGGAAA 372
κ-OR   RQSTNRVRNTVQDPASMRDVGGMNKPV 380
```

FIG. 2B

3H-METHADONE BINDING TO COS-7 MEMBRANES

3H-METHADONE BINDING TO LC132 IN COS-7 MEMBRANES

FIG. 7

Tyr-Gly-Gly-Phe-Thr-Gly-Ala-Arg-Lys-Ser-Ala-Arg-Lys-Leu-Ala-Asn-Gln    Orphanin FQ
Tyr-Gly-Gly-Phe-Leu-Arg-Arg-Ile-Arg-Pro-Lys-Leu-Lys-Trp-Asp-Asn-Gln    Dynorphin A
Tyr-Gly-Gly-Phe-Met-Thr-Ser-Glu-Lys-Ser-Gln-Thr-Pro-Leu-Val-Thr        α-Endorphin
Tyr-Gly-Gly-Phe-Leu-Arg-Arg-Gln-Phe-Lys-Val-Val-Thr                    Dynorphin B
Tyr-Gly-Gly-Phe-Leu                                                     Leu-Enkephalin

SEQUENCE LISTING

```
<160> NUMBER OF SEQ ID NOS: 15

<210> SEQ ID NO 1
<211> LENGTH: 31
<212> TYPE: DNA
<213> ORGANISM: Artificial Sequence
<220> FEATURE:
<223> OTHER INFORMATION: Description of Artificial  Sequence: primer
<221> NAME/KEY: misc_feature
<222> LOCATION: (1)..(31)
<223> OTHER INFORMATION: r represents g or a ; s represents g or c; y
      represents t/u or c; h represent s a or c or t/u
<221> NAME/KEY: modified_base
<222> LOCATION: (11)
<223> OTHER INFORMATION: n represents inosine

<400> SEQUENCE: 1
atgaattcac nrtsatgagy gtsgachght a                                      31

<210> SEQ ID NO 2
<211> LENGTH: 24
<212> TYPE: DNA
<213> ORGANISM: Artificial Sequence
<220> FEATURE:
<223> OTHER INFORMATION: Description of Artificial  Sequence: primer
<221> NAME/KEY: modified_base
<222> LOCATION: (19)
<223> OTHER INFORMATION: n represents inosine
<221> NAME/KEY: misc_feature
<222> LOCATION: (1)..(24)
<223> OTHER INFORMATION: r represents g or a ; y represents t/u or c

<400> SEQUENCE: 2
ttgtcgacrt arragrayng grtt                                              24

<210> SEQ ID NO 3
<211> LENGTH: 1452
<212> TYPE: DNA
<213> ORGANISM: Rattus sp.
<220> FEATURE:
<221> NAME/KEY: 5'UTR
<222> LOCATION: (1)..(181)
<221> NAME/KEY: CDS
<222> LOCATION: (182)..(1282)
```

```
<221> NAME/KEY: 3'UTR
<222> LOCATION: (1283)..(1452)

<400> SEQUENCE: 3
ccgaggagcc attcccagcc gcagcagacc ccaatctaga gtgagagtca t tgctcagtc      60 cactgtgctc ctgcctgccc gcctttctgc taagcattgg ggtctatttt g cgcccagct     120 tctgaagagg ctgtgtgtgc cgttggagga actgtactga gtggctttgc a gggtgacag     180 c atg gag tcc ctc ttt cct gct cca tac tgg  gag gtc ttg cat ggc agc     229
  Met Glu Ser Leu Phe Pro Ala Pro Tyr Trp  Glu Val Leu His Gly Ser
  1               5                   10                  15 cac ttt caa ggg aac ctg tcc ctc cta aat g ag acc gta ccc cac cac       277
His Phe Gln Gly Asn Leu Ser Leu Leu Asn G lu Thr Val Pro His His
                20                  25                  30 ctg ctc ctc aat gct agt cac agc gcc ttc c tg ccc ctt gga ctc aag       325
Leu Leu Leu Asn Ala Ser His Ser Ala Phe L eu Pro Leu Gly Leu Lys
            35                  40                  45 gtc acc atc gtg ggg ctc atc ttg gct gtg t gc atc ggg ggg ctc ctg       373
Val Thr Ile Val Gly Leu Ile Leu Ala Val C ys Ile Gly Gly Leu Leu
        50                  55                  60 ggg aac tgc ctc gtc atg tat gtc atc ctc a gg aca ccc aag atg aag       421
Gly Asn Cys Leu Val Met Tyr Val Ile Leu A rg Thr Pro Lys Met Lys
65                  70                  75                  80 aca gct acc aac att tac ata ttt aat ctg g ca ctg gct gat acc ctg       469
Thr Ala Thr Asn Ile Tyr Ile Phe Asn Leu A la Leu Ala Asp Thr Leu
                85                  90                  95 gtc ttg cta aca ctg ccc ttc cag ggc aca g ac atc cta ctg ggc ttc       517
Val Leu Leu Thr Leu Pro Phe Gln Gly Thr A sp Ile Leu Leu Gly Phe
            100                 105                 110 tgg cca ttt ggg aaa gca ctc tgc aag act g tc att gct atc gac tac       565
Trp Pro Phe Gly Lys Ala Leu Cys Lys Thr V al Ile Ala Ile Asp Tyr
        115                 120                 125 tac aac atg ttt acc agc act ttt act ctg a cc gcc atg agc gta gac       613
Tyr Asn Met Phe Thr Ser Thr Phe Thr Leu T hr Ala Met Ser Val Asp
    130                 135                 140 cgc tat gtg gct atc tgc cac cct atc cgt g cc ctt gat gtt cgg aca       661
Arg Tyr Val Ala Ile Cys His Pro Ile Arg A la Leu Asp Val Arg Thr
145                 150                 155                 160 tcc agc aaa gcc cag gct gtt aat gtg gcc a ta tgg gcc ctg gct tca       709
Ser Ser Lys Ala Gln Ala Val Asn Val Ala I le Trp Ala Leu Ala Ser
                165                 170                 175 gtg gtt ggt gtt cct gtt gcc atc atg ggt t ca gca caa gtg gaa gat       757
Val Val Gly Val Pro Val Ala Ile Met Gly S er Ala Gln Val Glu Asp
            180                 185                 190 gaa gag atc gag tgc ctg gtg gag atc cct g cc cct cag gac tat tgg       805
Glu Glu Ile Glu Cys Leu Val Glu Ile Pro A la Pro Gln Asp Tyr Trp
        195                 200                 205 ggc cct gta ttc gcc atc tgc atc ttc ctt t tt tcc ttc atc atc cct       853
Gly Pro Val Phe Ala Ile Cys Ile Phe Leu P he Ser Phe Ile Ile Pro
    210                 215                 220 gtg ctg atc atc tct gtc tgc tac agc ctc a tg att cga cga ctt cgt       901
Val Leu Ile Ile Ser Val Cys Tyr Ser Leu M et Ile Arg Arg Leu Arg
225                 230                 235                 240 ggt gtc cgt ctg ctt tca ggc tcc cgg gag a ag gac cga aac ctg cgg       949
Gly Val Arg Leu Leu Ser Gly Ser Arg Glu L ys Asp Arg Asn Leu Arg
                245                 250                 255 cgt atc act cga ctg gtg ctg gta gtg gtg g ct gtg ttt gtg ggc tgc       997
Arg Ile Thr Arg Leu Val Leu Val Val Val A la Val Phe Val Gly Cys
            260                 265                 270
```

-continued

```
tgg acg cct gtg cag gtg ttt gtc ctg gtt c aa gga ctg ggt gtt cag      1045
Trp Thr Pro Val Gln Val Phe Val Leu Val G ln Gly Leu Gly Val Gln
        275                 280                 285 cca ggt agt gag act gca gtt gcc atc ctg c gc ttc tgc aca gcc ctg      1093
Pro Gly Ser Glu Thr Ala Val Ala Ile Leu A rg Phe Cys Thr Ala Leu
    290                 295                 300 ggc tat gtc aac agt tgt ctc aat ccc att c tc tat gct ttc ctg gat      1141
Gly Tyr Val Asn Ser Cys Leu Asn Pro Ile L eu Tyr Ala Phe Leu Asp
305                 310                 315                 320 gag aac ttc aag gcc tgc ttt aga aag ttc t gc tgt gct tca tcc ctg      1189
Glu Asn Phe Lys Ala Cys Phe Arg Lys Phe C ys Cys Ala Ser Ser Leu
                325                 330                 335 cac cgg gag atg cag gtt tct gat cgt gtg c gg acg att gcc aag gat      1237
His Arg Glu Met Gln Val Ser Asp Arg Val A rg Thr Ile Ala Lys Asp
            340                 345                 350 gtt ggc ctt ggt tgc aag act tct gag aca g ta cca cgg cca gca           1282
Val Gly Leu Gly Cys Lys Thr Ser Glu Thr V al Pro Arg Pro Ala
        355                 360                 365 tgactaggcg tggacctgcc catggtgcct gtcagcccac agagcccatc c tacacccaa    1342 cacggagctc acacaggtca ctgctctcta ggttgaccct gaaccttgag c atctggagc    1402 cttgaatggc ttttcttttg gatcaggatg ctcagtccta gaggaagacc                1452
```

<210> SEQ ID NO 4
<211> LENGTH: 367
<212> TYPE: PRT
<213> ORGANISM: Rattus sp.

<400> SEQUENCE: 4

```
Met Glu Ser Leu Phe Pro Ala Pro Tyr Trp G lu Val Leu His Gly Ser
1               5                   10                  15

His Phe Gln Gly Asn Leu Ser Leu Leu Asn G lu Thr Val Pro His His
            20                  25                  30

Leu Leu Leu Asn Ala Ser His Ser Ala Phe L eu Pro Leu Gly Leu Lys
        35                  40                  45

Val Thr Ile Val Gly Leu Ile Leu Ala Val C ys Ile Gly Gly Leu Leu
    50                  55                  60

Gly Asn Cys Leu Val Met Tyr Val Ile Leu A rg Thr Pro Lys Met Lys
65                  70                  75                  80

Thr Ala Thr Asn Ile Tyr Ile Phe Asn Leu A la Leu Ala Asp Thr Leu
                85                  90                  95

Val Leu Leu Thr Leu Pro Phe Gln Gly Thr A sp Ile Leu Leu Gly Phe
            100                 105                 110

Trp Pro Phe Gly Lys Ala Leu Cys Lys Thr V al Ile Ala Ile Asp Tyr
        115                 120                 125

Tyr Asn Met Phe Thr Ser Thr Phe Thr Leu T hr Ala Met Ser Val Asp
    130                 135                 140

Arg Tyr Val Ala Ile Cys His Pro Ile Arg A la Leu Asp Val Arg Thr
145                 150                 155                 160

Ser Ser Lys Ala Gln Ala Val Asn Val Ala I le Trp Ala Leu Ala Ser
                165                 170                 175

Val Val Gly Val Pro Val Ala Ile Met Gly S er Ala Gln Val Glu Asp
            180                 185                 190

Glu Glu Ile Glu Cys Leu Val Glu Ile Pro A la Pro Gln Asp Tyr Trp
        195                 200                 205

Gly Pro Val Phe Ala Ile Cys Ile Phe Leu P he Ser Phe Ile Ile Pro
    210                 215                 220
```

```
Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
            245                 250                 255

Arg Ile Thr Arg Leu Val Leu Val Val Ala Val Phe Val Gly Cys
                260             265                 270

Trp Thr Pro Val Gln Val Phe Val Leu Val Gln Gly Leu Gly Val Gln
            275                 280                 285

Pro Gly Ser Glu Thr Ala Val Ala Ile Leu Arg Phe Cys Thr Ala Leu
        290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ser Leu
                325                 330                 335

His Arg Glu Met Gln Val Ser Asp Arg Val Arg Thr Ile Ala Lys Asp
            340                 345                 350

Val Gly Leu Gly Cys Lys Thr Ser Glu Thr Val Pro Arg Pro Ala
        355                 360                 365

<210> SEQ ID NO 5
<211> LENGTH: 17
<212> TYPE: PRT
<213> ORGANISM: Artificial Sequence
<220> FEATURE:
<223> OTHER INFORMATION: Description of Artificial  Sequence: peptide ligand

<400> SEQUENCE: 5

Phe Gly Gly Phe Thr Gly Ala Arg Lys Ser Ala Arg Lys Leu Ala Asn
1               5                   10                  15

Gln

<210> SEQ ID NO 6
<211> LENGTH: 17
<212> TYPE: PRT
<213> ORGANISM: Artificial Sequence
<220> FEATURE:
<223> OTHER INFORMATION: Description of Artificial  Sequence: peptide
      ligand

<400> SEQUENCE: 6

Phe Gly Gly Phe Thr Gly Ala Arg Lys Ser Ala Arg Lys Tyr Ala Asn
1               5                   10                  15

Gln

<210> SEQ ID NO 7
<211> LENGTH: 398
<212> TYPE: PRT
<213> ORGANISM: Rattus sp.

<400> SEQUENCE: 7

Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Ala Gly Asn Asp Ser Leu Cys Pro Gln Thr Gly Ser Pro Ser
    50                  55                  60
```

-continued

```
Met Val Thr Ala Ile Thr Ile Met Ala Leu Tyr Ser Ile Val Cys Val
 65                  70                  75                  80

Val Gly Leu Phe Gly Met Phe Leu Val Met Tyr Val Ile Val Arg Tyr
                 85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Met Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Lys Lys Asp
            260                 265                 270

Arg Asn Leu Arg Arg Ile Thr Arg Met Val Leu Val Val Val Ala Val
        275                 280                 285

Thr Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Met Ser Cys Leu Met Pro Val Leu Tyr
                325                 330                 335

Ala Phe Leu Asp Lys Met Thr Lys Arg Cys Thr Arg Glu Phe Cys Ile
            340                 345                 350

Pro Thr Ser Ser Thr Ile Glu Gln Gln Asn Ser Thr Arg Val Arg Gln
        355                 360                 365

Asn Thr Arg Glu His Pro Ser Thr Ala Asn Thr Val Asp Arg Thr Asn
    370                 375                 380

His Gln Leu Glu Asn Leu Glu Ala Glu Thr Ala Pro Leu Pro
385                 390                 395
```

<210> SEQ ID NO 8
<211> LENGTH: 372
<212> TYPE: PRT
<213> ORGANISM: Mus sp.

<400> SEQUENCE: 8

```
Met Glu Leu Val Pro Ser Ala Arg Ala Glu Leu Gln Ser Ser Pro Leu
  1               5                  10                  15

Val Asn Leu Ser Asp Ala Phe Pro Ser Ala Phe Pro Ser Ala Gly Ala
                 20                  25                  30

Asn Ala Ser Gly Ser Pro Gly Ala Arg Ser Ala Ser Ser Leu Ala Leu
             35                  40                  45
```

```
Ala Ile Ala Ile Thr Ala Leu Tyr Ser Ala Val Cys Ala Val Gly Leu
     50                  55                  60
Leu Gly Met Val Leu Val Met Phe Gly Ile Val Arg Tyr Thr Lys Leu
 65                  70                  75                  80
Lys Thr Ala Thr Asn Ile Tyr Ile Phe Met Leu Ala Leu Ala Asp Ala
                 85                  90                  95
Leu Ala Thr Ser Thr Leu Pro Phe Gln Ser Ala Lys Tyr Leu Met Glu
                100                 105                 110
Thr Trp Pro Phe Gly Glu Leu Leu Cys Lys Ala Val Leu Ser Ile Asp
            115                 120                 125
Tyr Tyr Lys Met Thr Thr Ser Ile Phe Thr Leu Thr Met Met Ser Val
130                 135                 140
Asp Arg Tyr Ile Ala Val Cys His Pro Val Lys Ala Leu Asp Phe Arg
145                 150                 155                 160
Thr Pro Ala Lys Ala Lys Leu Ile Met Ile Cys Ile Trp Val Leu Ala
                165                 170                 175
Ser Gly Val Gly Val Pro Ile Met Val Met Ala Val Thr Gln Pro Arg
                180                 185                 190
Asp Phe Ala Val Val Cys Met Leu Gln Phe Pro Ser Pro Ser Trp Tyr
            195                 200                 205
Trp Asp Thr Val Thr Lys Ile Cys Val Phe Leu Phe Ala Phe Val Val
        210                 215                 220
Pro Ile Leu Ile Ile Thr Val Cys Tyr Gly Leu Met Leu Leu Arg Leu
225                 230                 235                 240
Arg Ser Val Arg Leu Leu Ser Gly Ser Lys Lys Lys Asp Arg Ser Leu
                245                 250                 255
Arg Arg Ile Thr Arg Met Val Leu Val Val Val Gly Ala Phe Val Val
                260                 265                 270
Cys Trp Ala Pro Ile His Ile Phe Val Ile Val Trp Thr Leu Val Asp
            275                 280                 285
Ile Asn Arg Arg Asp Pro Leu Val Val Ala Ala Leu His Leu Cys Ile
        290                 295                 300
Ala Leu Gly Tyr Ala Met Ser Ser Leu Met Pro Val Leu Tyr Ala Phe
305                 310                 315                 320
Leu Asp Lys Lys Thr Lys Arg Cys Thr Arg Gln Leu Cys Arg Thr Pro
                325                 330                 335
Cys Gly Arg Gln Glu Pro Gly Ser Leu Arg Arg Pro Arg Gln Ala Thr
                340                 345                 350
Thr Arg Glu Arg Val Thr Ala Cys Thr Pro Ser Asp Gly Pro Gly Gly
            355                 360                 365
Gly Ala Ala Ala
        370

<210> SEQ ID NO 9
<211> LENGTH: 378
<212> TYPE: PRT
<213> ORGANISM: Mus sp.

<400> SEQUENCE: 9

Met Glu Ser Pro Ile Gln Ile Phe Arg Gly Asp Pro Gly Pro Thr Cys
 1               5                  10                  15
Ser Pro Ser Ala Cys Leu Leu Pro Asn Ser Ser Ser Trp Phe Pro Asn
                 20                  25                  30
Trp Ala Glu Ser Asp Ser Asn Gly Ser Val Gly Ser Glu Asp Gln Gln
```

```
            35                  40                  45
Leu Glu Ser Ala His Ile Ser Pro Ala Ile Pro Val Ile Ile Thr Ala
    50                  55                  60
Val Tyr Ser Val Val Phe Val Val Gly Leu Val Gly Met Ser Leu Val
 65                  70                  75                  80
Met Phe Val Ile Ile Arg Tyr Thr Lys Met Lys Thr Ala Thr Asn Ile
                 85                  90                  95
Tyr Ile Phe Met Leu Ala Leu Ala Asp Ala Leu Val Thr Thr Thr Met
                100                 105                 110
Pro Phe Gln Ser Ala Val Tyr Leu Met Asn Ser Trp Pro Phe Gly Asp
                115                 120                 125
Val Leu Cys Lys Ile Val Ile Ser Ile Asp Tyr Lys Lys Phe Thr Ser
    130                 135                 140
Ile Phe Thr Leu Thr Met Met Ser Val Asp Arg Tyr Ile Ala Val Cys
145                 150                 155                 160
His Pro Val Lys Ala Leu Asp Phe Arg Thr Pro Leu Lys Ala Lys Ile
                165                 170                 175
Ile Trp Ile Cys Ile Trp Leu Leu Ala Ser Ser Val Gly Ile Ser Ala
                180                 185                 190
Ile Val Leu Gly Gly Thr Lys Val Arg Glu Asp Val Asp Val Ile Glu
    195                 200                 205
Cys Ser Leu Phe Pro Asp Asp Glu Tyr Ser Trp Trp Asp Leu Phe Met
210                 215                 220
Lys Ile Cys Val Phe Val Phe Ala Phe Val Ile Pro Val Leu Ile Ile
225                 230                 235                 240
Ile Val Cys Tyr Thr Leu Met Ile Leu Arg Leu Lys Ser Val Arg Leu
                245                 250                 255
Leu Ser Gly Ser Arg Lys Lys Asp Arg Asn Leu Arg Arg Ile Thr Lys
                260                 265                 270
Leu Val Leu Val Val Val Ala Val Phe Ile Ile Cys Asn Thr Pro Ile
    275                 280                 285
His Ile Phe Ile Leu Val Glu Ala Leu Gly Ser Thr Ser His Ser Thr
    290                 295                 300
Ala Ala Leu Ser Ser Tyr Tyr Phe Cys Ile Ala Leu Gly Tyr Thr Met
305                 310                 315                 320
Ser Ser Leu Met Pro Val Leu Tyr Ala Phe Leu Asp Lys Asn Phe Lys
                325                 330                 335
Arg Cys Thr Arg Asp Phe Cys Phe Pro Ile Lys Met Arg Met Glu Arg
                340                 345                 350
Gln Ser Thr Asn Arg Val Arg Asn Thr Val Gln Asp Pro Ala Ser Met
                355                 360                 365
Arg Asp Val Gly Gly Met Asn Lys Pro Val
    370                 375

<210> SEQ ID NO 10
<211> LENGTH: 17
<212> TYPE: PRT
<213> ORGANISM: Artificial Sequence
<220> FEATURE:
<223> OTHER INFORMATION: Description of Artificial  Sequence: opioid
      peptide

<400> SEQUENCE: 10

Tyr Gly Gly Phe Leu Arg Arg Ile Arg Pro Lys Leu Lys Trp Asp Asn
 1               5                  10                  15
```

Gln

```
<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: alpha
      endorphin peptide

<400> SEQUENCE: 11

Tyr Gly Gly Phe Met Thr Ser Glu Lys Ser Gln Thr Pro Leu Val Thr
 1               5                  10                  15

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: dynorphin B
      peptide

<400> SEQUENCE: 12

Tyr Gly Gly Phe Leu Arg Arg Gln Phe Lys Val Val Thr
 1               5                  10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:
      Leu-Enkephalin peptide

<400> SEQUENCE: 13

Tyr Gly Gly Phe Leu
 1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 14

Phe Gly Gly Phe
 1

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: peptide
      which binds to a mammalian opioid receptor.
<221> NAME/KEY: SITE
<222> LOCATION: (1)
<223> OTHER INFORMATION: Xaa is any amino acid wherein the sum of the
      amino acids present at position 1 and position 19 does not exceed
      82.
<221> NAME/KEY: SITE
<222> LOCATION: (6)
<223> OTHER INFORMATION: Xaa is Thr, Leu, or Met
<221> NAME/KEY: SITE
<222> LOCATION: (7)
<223> OTHER INFORMATION: Xaa is Gly, Arg, or Thr
<221> NAME/KEY: SITE
<222> LOCATION: (8)
<223> OTHER INFORMATION: Xaa is Ala, Arg, or Ser
```

-continued

```
<221> NAME/KEY: SITE
<222> LOCATION: (9)
<223> OTHER INFORMATION: Xaa is Arg, Ile,  Glu, or Gln
<221> NAME/KEY: SITE
<222> LOCATION: (10)
<223> OTHER INFORMATION: Xaa is Lys, Arg, or  Phe
<221> NAME/KEY: SITE
<222> LOCATION: (11)
<223> OTHER INFORMATION: Xaa is Ser, Pro, or  Lys
<221> NAME/KEY: SITE
<222> LOCATION: (12)
<223> OTHER INFORMATION: Xaa is Ala, Lys, Gl n, or Val
<221> NAME/KEY: SITE
<222> LOCATION: (13)
<223> OTHER INFORMATION: Xaa is Arg, Leu, Th r or Val
<221> NAME/KEY: SITE
<222> LOCATION: (14)
<223> OTHER INFORMATION: Xaa is Lys, Pro, or  Thr
<221> NAME/KEY: SITE
<222> LOCATION: (15)
<223> OTHER INFORMATION: Xaa is Tyr, Leu, or  Trp
<221> NAME/KEY: SITE
<222> LOCATION: (16)
<223> OTHER INFORMATION: Xaa is Ala, Asp, or  Val
<221> NAME/KEY: SITE
<222> LOCATION: (17)
<223> OTHER INFORMATION: Xaa is Asn or Thr
<221> NAME/KEY: SITE
<222> LOCATION: (19)
<223> OTHER INFORMATION: Xaa is any amino ac id wherein the sum of the
      amino acids present at position 1 and position 19 does not exceed
      82.

<400> SEQUENCE: 15

Xaa Phe Gly Gly Phe Xaa Xaa Xaa Xaa X aa Xaa Xaa Xaa Xaa Xaa
  1               5                   10                  15

Xaa Gln Xaa
```

METHOD OF SCREENING OF A COMPOUND FOR BINDING TO MSOR

This application is a divisional of U.S. Ser. No. 08/514,451, filed Aug. 11, 1995, issued as U.S. Pat. No. 5,837,809 on Nov. 17, 1998, which is a is a continuation-in-part of U.S. Ser. No. 08/149,093, filed Nov. 8, 1993, issued as U.S. Pat. No. 5,658,783 on Aug. 19, 1997, the disclosure of which are incorporated in their entirety herein.

This invention was made with government support under National Institute of Health grants R01 MH48991. The government has certain rights to this invention.

BACKGROUND OF THE INVENTION

1. Field of the Invention

This invention relates to opioid receptors from mammalian species and ligands specific for such receptors. Specifically, the invention relates to the isolation of an endogenous peptide ligand specific for a novel mammalian opioid receptor. The invention also relates to the construction of analogues, derivatives and peptide mimetics of this endogenous mammalian opioid receptor ligand. Specifically provided is a mammalian hypothalamus-derived endogenous opioid receptor ligand, synthetic embodiments and analogues thereof. Methods of making and using such ligands, as well as antibodies against and epitopes of this novel opioid receptor ligand are also provided by the invention.

2. Background of the Invention

The use (and abuse) of opiates, archetypally opium and morphine, have been known since antiquity (reviewed in Brownstein, 1993, Proc. Natl. Acad. Sci. USA 90: 5391–5393). Since the nineteenth century, chemical characterization and synthesis of a number of morphine analogues have been achieved in an effort to discover a compound with the analgesic effects of morphine that lacks or is substantially attenuated in its addictive potential. These efforts have proven fruitless to date.

The biology behind the reasons why morphine and morphine-like compounds display both analgesic and addictive properties was first elucidated by the discovery of endogenous morphine-like compounds termed enkephalins (see DiChara & North, 1992, Trends in Pharmacol. Sci. 13: 185–193 for review). Accompanying this finding of an endogenous opiate was the biochemical evidence for a family of related but distinct opiate receptors, each of which displays a unique pharmacological profile of response to opiate agonists and antagonists (see McKnight & Rees, 1991, Neurotransmissions 7: 1–6 for review). To date, four distinct opiate receptors have been described by their pharmacological profiles and anatomical distribution: these comprise the $\mu$, $\delta$, $\kappa$ and $\sigma$ receptors (the $\sigma$ receptor has been determined to be a non-opioid receptor with cross-reactivity to some opioid agonists).

Thus, mammalian opioid receptors are known in the art, and some of these proteins have been isolated biochemically and their corresponding genes have been recently cloned using genetic engineering means.

Kieffer et al., 1992, Proc. Natl. Acad. Sci. USA 89: 12048–12052 disclosed the isolation of a cDNA copy of the mouse $\delta$-opioid receptor by expression cloning.

Evans et al., 1992, Science 258: 1952–1955 disclose the isolation of a cDNA copy of the mouse $\delta$-opioid receptor by expression cloning.

Chen et al., 1993, Molec. Pharmacol. 44: 8–12 disclose the isolation of a cDNA copy of the rat $\mu$-opioid receptor.

Yasuda et al., 1993, Proc. Natl. Acad. Sci. USA 90: 6736–6740 disclose the isolation of a cDNA copy of each of the mouse $\kappa$- and $\delta$-opioid receptor.

Bzdega et al., 1993, Proc. Natl. Acad. Scd. USA 90: 9305–9309 disclose the isolation and chromosomal location of the $\delta$-opioid receptor in the mouse.

The present inventors have cloned, expressed and functionally characterized a novel mammalian opioid receptor gene, disclosed in co-owned and co-pending U.S. patent application, Ser. No. 08/149,093, filed Nov. 8, 1993, and issued as U.S. Pat. No. 5,658,783 on Aug. 19, 1997 which is hereby incorporated by reference in its entirety. Specifically disclosed therein are nucleic acids encoding the novel mammalian opioid receptor gene, recombinant expression constructs comprising this opioid receptor gene, cells containing such constructs and expressing the novel opioid receptor gene, and methods for making and using such nucleic acids, constructs and cells for opioid detection and novel drug screening. The nucleic acid sequence of the MSOR gene and the deduced amino acid sequence of the cognate receptor protein were also disclosed in this prior application.

In 1991, U.S. pharmaceutical companies spent an estimated $7.9 billion on research and development devoted to identifying new therapeutic agents (Pharmaceutical Manufacturer's Association). The magnitude of this amount is due, in part, to the fact that the hundreds, if not thousands, of chemical compounds must be tested in order to identify a single effective therapeutic agent that does not engender unacceptable levels of undesirable or deleterious side effects. There is an increasing need for economical methods of testing large numbers of chemical compounds to quickly identify those compounds that are likely to be effective in treating disease.

This is of particular importance for psychoactive and psychotropic drugs, due to their pharmacological importance and their potential to greatly benefit or greatly harm human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. For these and other reasons, development of in vitro screening methods for psychotropic drugs has numerous advantages and is a major research goal in the pharmaceutical industry. The ability to synthesize human opioid receptor molecules in vitro would represent one way to provide an efficient and economical means for rational drug design and rapid screening of potentially useful compounds.

A great advantage in efforts for developing novel psychotropic drugs which exert their activity (analgesic and otherwise) aria binding to mammalian opioid receptors would be to identify the endogenous ligand(s) which bind to such receptors. Certain such ligands have been isolated in the prior art, including the peptides comprising the endorphins and enkephalins (see Jaffe and Martin, 1990, "Opioid Analgesics and Antagonists", in Goodman and Gilman, eds., *The Pharmacological Basis of Therapeutics,* 8th ed. (Pergammon Press, Inc.: New York), Chapter 21, p.485–521). The identification and characterization of additional endogenous ligands would advantageously provide another basis for rational drug design and an appreciation for structural features of such ligands both shared with other opioid receptor ligands and unique for ligands specific for individual receptors or subclasses of receptors.

SUMMARY OF THE INVENTION

This invention provides small, readily-produced peptides that are ligands for a novel mammalian opioid receptor protein having the amino acid sequence identified as SEQ ID Nos.: 5 and 6. Peptides of the invention are characterized as having an amino acid sequence that is the amino acid sequence identified as SEQ ID Nos.: 5 and 6 or a subsequence thereof, amino acid sequence variants of the sequence or subsequence, as well as analogues and derivatives thereof, that are ligands for the novel mammalian opioid receptor protein having the amino acid sequence identified as SEQ ID Nos.: 5 and 6, as well as analogues and derivative thereof.

The peptides of the invention include linear and cyclized peptides, and synthetic analogues and variants thereof. Certain embodiments of such variants include, substitution variants, wherein an amino acid residue at one or more positions in the peptide is replaced with a different amino acid residue (including atypical amino acid residues) from that found in the corresponding position of amino acid sequence of the parent peptide of the invention. In a preferred embodiment, the substituted amino acid is tyrosine. Certain other embodiments of peptide variants of the invention include addition variants, wherein such variant peptides may include up to about a total of 10 additional amino acids, covalently linked to either the amino-terminal or carboxyl-terminal extent, or both, of the parent, opioid receptor binding peptide of provided by the invention. Such additional amino acids may also include atypical amino acids. Linear and cyclized embodiments of the amino acid substitution and addition variant peptides are also provided as peptides of the invention. In addition, peptides of the invention may be provided as fusion proteins with other functional targeting agents, such as immunoglobulin fragments. Derivatives of the peptides of the invention also include modifications of the amino- and carboxyl-termini and amino acid side chain chemical groups such as amines, carboxylic acids, alkyl and phenyl groups.

In a first aspect, the invention provides peptides of the formula: $(Xaa)_n$-Phe-Gly-Gly-Phe-$(A^1)$-$(A^2)$-$(A^3)$-$(A^4)$-$(A^5)$-$(A^6)$-$(A^7)$-$(A^8)$-$(A^9)$-$(A^{10})$-$(A^{11})$-$(A^{12})$-Gln-$(Xaa)_m$ wherein $A^1$ is Thr, Leu or Met; $A^2$ is Gly, Arg or Thr; $A^3$ is Ala, Arg or Ser; $A^4$ is Arg, Ile, Glu or Gln; $A^5$ is Lys, Arg or Phe; $A^6$ is Ser, Pro or Lys; $A^7$ is Ala, Lys, Gln or Val; $A^8$ is Arg, Leu, Thr or Val; $A^9$ is Lys, Pro or Thr; $A^{10}$ is Tyr, Leu or Trp; $A^{11}$ is Ala, Asp or Val; $A^{12}$ is Asn. or Thr; (Xaa) is any amino acid; n and m are integers wherein n+m is no more than 82(SEQ ID No.:15); and the amino acids are each individually in either the D or L stereochemical configuration and the peptide specifically binds to a mammalian opioid receptor having an amino acid sequence identified by Seq ID Nos.:4. In a preferred embodiment, the peptide has the formula:

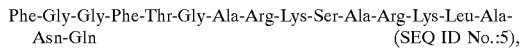
Phe-Gly-Gly-Phe-Thr-Gly-Ala-Arg-Lys-Ser-Ala-Arg-Lys-Leu-Ala-Asn-Gln (SEQ ID No.:5), and n+m equals zero. In an another preferred embodiment, the peptide has the formula:

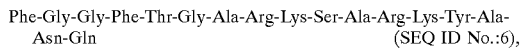
Phe-Gly-Gly-Phe-Thr-Gly-Ala-Arg-Lys-Ser-Ala-Arg-Lys-Tyr-Ala-Asn-Gln (SEQ ID No.:6), and n+m equals zero. Both naturally-occurring embodiments of such peptides, purified using well-established techniques from the cells or tissues producing the peptide, and synthetic embodiments, are within the scope of the invention.

In other embodiments of this aspect of the invention are provided peptides of general formula:

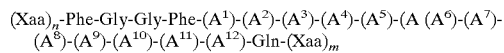
$(Xaa)_n$-Phe-Gly-Gly-Phe-$(A^1)$-$(A^2)$-$(A^3)$-$(A^4)$-$(A^5)$-$(A^6)$-$(A^7)$-$(A^8)$-$(A^9)$-$(A^{10})$-$(A^{11})$-$(A^{12})$-Gln-$(Xaa)_m$ and having amino acid substituents as described above wherein such peptides are radiolabeled by conjugation with or binding to a radioactive isotope. In a preferred embodiment, the peptide has the formula:

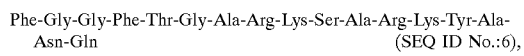
Phe-Gly-Gly-Phe-Thr-Gly-Ala-Arg-Lys-Ser-Ala-Arg-Lys-Tyr-Ala-Asn-Gln (SEQ ID No.:6), n+m equals zero, and the radiolabel is a radioisotope of iodine. In other preferred embodiments, the peptide is covalently linked to a radiolabel binding moiety and the radiolabel a radioisotope of indium, gallium, technetium, rhenium or other useful radioisotope.

The invention also provides pharmaceutical compositions of the peptides of the invention. In a first aspect, the peptides of the invention are provided in a pharmaceutical composition comprising an acceptable carrier or diluent. In a second aspect, such pharmaceutical compositions are provided in detectably-labeled embodiments, useful for diagnostic identification of sites of both normal and pathological peptide ligand receptor binding in vivo and in vitro. In such embodiments, the peptides of the invention are detectably labeled, for example, with a radioisotope such as I-123, 1–125 or I-131, conjugated to the peptide via, inter alia, a tyrosine residue that is non-essential for receptor binding. Additional radioisotopes, such as In-111, Ga-67, Re-186, Re-188 and Tc-99m, can be conjugated to such peptides using methods well-understood in the art. In such embodiments, the pharmaceutical composition is radiolabeled to an appropriate specific activity, and administered to an animal, preferably a human, at a diagnostically-effective and non-toxic dose. Methods and routes of administration may be selected by those with skill in the art based on well-established techniques and in a clinically-appropriate fashion.

In a second aspect of the pharmaceutical compositions of the invention, the opioid receptor-binding ligand peptides are provided in an appropriate composition with acceptable carriers of diluents and in a therapeutically-effective amount. In such embodiments, the therapeutic pharmaceutical compositions are used in methods to treat diseases or pathological conditions associated with ligand binding to the MSOR receptor. Specifically provided are methods for treating locomotor diseases in an animal.

The invention also provides methods for designing MSOR opioid receptor ligands and analogues, derivatives and mimetics thereof, using the amino acid sequence of the peptide ligands of the invention. Also encompassed within the scope of this invention are such analogues, derivatives and mimetics produced by the methods of the invention.

In a second aspect, the invention provides nucleic acids encoding a novel mammalian opioid-specific receptor protein having an amino acid sequence identified as SEQ ID No.:4, recombinant eukaryotic expression constructs capable of expressing the novel mammalian opioid-specific receptor of the invention in cultures of transformed cells, as well as cultures of transformed eukaryotic cells that synthesize the receptor of the invention. The invention also provides homogeneous compositions of the receptor protein having an amino acid sequence identified as SEQ ID No.:4, and antibodies against and epitopes of the receptor protein of the invention. Methods for characterizing these receptor proteins and methods for using these proteins in the development of agents having pharmacological uses related to these receptors are also provided by the invention.

In this aspect of the invention is provided a nucleic acid having a nucleotide sequence encoding a mammalian MSOR opioid receptor. In a preferred embodiment, the nucleic acid encodes 1452 nucleotides of the cDNA comprising 1101 nucleotides of coding sequence, 181 nucleotides, of 5' untranslated sequence and 170 nucleotides of 3' untranslated sequence, depicted in FIGS. 1A and 1B and identified as SEQ ID No:3. Encompassed in this aspect of the invention is the disclosed sequence and allelic variants of this sequence, either naturally occurring or the product of in vitro chemical or genetic modification.

The corresponding receptor protein, having the deduced amino acid sequence shown in FIGS. 1A and 1B and identified as SEQ ID No.:4, is also an aspect of the invention. In particular embodiments of this aspect of the invention is comprised a homogeneous composition of the 47 kD mammalian opioid receptor protein and derivatives thereof, said size being understood to be the size of the protein before any post-translational modifications. The amino acid sequence of this 47 kD receptor protein is depicted in FIGS. 1A and 1B and identified as SEQ ID No:4.

This invention provides both nucleotide and amino acid sequence probes derived from the sequences herein provided, isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clones embodying this aspect of the invention, and oligonucleotide and other synthetic probes synthesized chemically using the nucleotide sequence information of cDNA or genomic clone embodiments of the invention.

The present invention also includes synthetic peptides made using the nucleotide sequence information comprising the cDNA embodiments of the receptor protein embodiments of the invention. The invention includes either naturally occurring or synthetic peptides which may be used as antigens for the production of receptor-specific antibodies, or useful as competitors of receptor molecules for agonist, antagonist or drug binding, or to be used for the production of inhibitors of the binding of agonists or antagonists or analogues -thereof to such MSOR receptor molecules. Particularly preferred embodiments of this aspect of the invention are such peptides that interact with the peptide ligand embodiments of the invention and enhance or inhibit peptide ligand binding to the receptor protein.

The present invention also provides antibodies against and epitopes of the mammalian opioid receptor molecules of the invention, including antisera and both polyclonal and monoclonal embodiments of such antibodies and hybridoma cell lines producing such monoclonal antibodies.

The present invention provides recombinant expression constructs comprising a nucleic acid encoding a mammalian MSOR receptor of the invention wherein the construct is capable of expressing the encoded MSOR receptor in cultures of cells transformed with the construct. Preferred embodiments of such constructs comprise the MSOR receptor cDNA depicted in FIGS. 1A and 1B (SEQ ID No.:3), such constructs being capable of expressing the MSOR receptor encoded therein in cells transformed with the construct.

The invention also provides cultures cells transformed with the recombinant expression constructs of the invention, each such cultures being capable of and in fact expressing the mammalian MSOR receptor encoded in the transforming construct.

The present invention also includes within its scope protein preparations of prokaryotic and eukaryotic cell membranes containing the MSOR receptor protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian MSOR receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known opioid agonists and antagonists, is assayed. Additional preferred embodiments comprise quantitative analyses of such effects. The invention specifically provides a method for screening a compound for a capacity to bind to a mammalian MSOR opioid receptor in cells expressing the receptor, using a competitive assay between the compound to be tested and the peptide ligands of the invention. The method comprises the steps of:

(a) transforming a culture of eukaryotic or prokaryotic cells with a recombinant expression construct capable of expressing a mammalian MSOR opioid receptor having an amino acid sequence identified as SEQ ID No.:4, wherein the cells of the transformed cell culture express the opioid receptor;

(b) assaying the transformed cell culture for binding of an amount of a detectably-labeled peptide according to claim 1 in competition with varying amounts of the compound; and (c) determining whether the compound competitively binds to the opioid receptor by calculating the extent of inhibition of binding of the detectably-labeled peptide in the presence of the compound.

In additional embodiments of this method is included the additional step of:

(d) comparing the binding capacity of the compound with the binding capacities of additional compounds that are known to bind to mammalian opioid receptors, wherein said additional compounds comprise naturally-occurring and synthetic opioid receptor agonists and antagonists.

The present invention is also useful for the detection of analogues, agonists or antagonists, known or unknown, of the mammalian MSOR receptors of the invention, either naturally occurring or embodied as a drug. In preferred embodiments, such analogues, agonists or antagonists may be detected in blood, saliva, semen, cerebrospinal fluid, plasma, lymph, or any other bodily fluid. In particularly preferred embodiments, the peptide ligands of the invention are used in competitive binding assays to quantitatively evaluate novel ligand binding to the MSOR receptor.

Specific preferred embodiments of the present invention will become evident from the following more detailed description of certain preferred embodiments and the claims.

DESCRIPTION OF THE DRAWINGS

FIGS. 1A and 1B illustrates the nucleotide (SEQ ID No.:3) and amino acid (SEQ ID No.:4) sequences of the novel mammalian MSOR opioid receptor of the invention.

FIGS. 2A and 2B presents an amino acid sequence comparison between the novel mammalian MSOR opioid receptor protein of the invention (SEQ ID No.:4 designated LCI32) and the rat μ-opioid receptor (SEQ ID No.:7), and the mouse δ- (SEQ ID No.:8) and κ-oploid (SEQ ID No.:9) receptor proteins.

FIG. 7 is a comparison of the amino acid sequence of orphanin FQ (SEQ ID No.:5) and other opioid receptor binding peptides (dynorphin A, SEQ ID No.:10; α-endorphin SEQ ID No.:11; dynorphin B, SEQ ID No.:12; and Leu-Enkephalin, SEQ ID No.:13); identical amino acid residues shared between the peptides are shown in boldface.

DETAILED DESCRIPTION OF THE PREFERRED EMBODIMENTS

Figure 3:
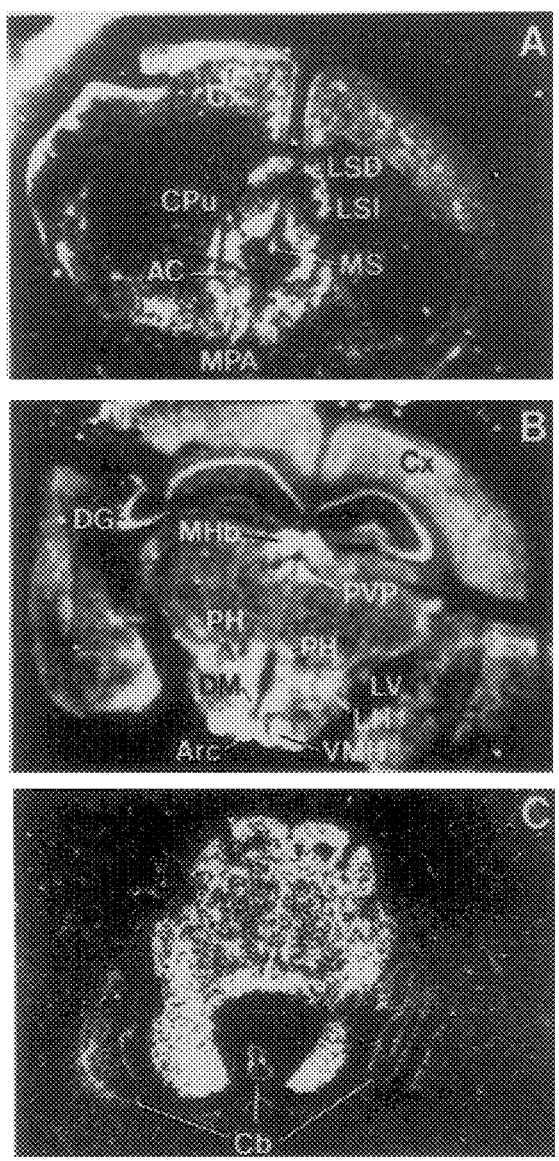
FIGS. 3A–3C illustrates in situ hybridization of rat brain sections with a nucleic acid hybridization probe specific for the mammalian MSOR opioid receptor of the invention.

The term ."novel mammalian opioid receptor" and "MSOR" as used herein refers to proteins consisting essentially of, and having substantially the same biological activity as, the protein encoded by the nucleic acid depicted FIGS. 1A and 1B (SEQ ID No.:3). This definition is intended to encompass natural allelic variations in the disclosed MSOR sequence. Cloned nucleic acid provided by the present invention may encode MSOR protein of any species of origin, including, for example, mouse, rat, rabbit, cat, and human, but preferably the nucleic acid provided by the invention encodes MSOR receptors of mammalian, most preferably rat and human, origin.

The nucleic acids of the invention comprise nucleic acid hybridization probes comprising DNA or RNA consisting essentially of the nucleotide sequence of the MSOR receptor, depicted FIGS. 1A and 1B (SEQ ID No.:3), or any portion thereof effective in nucleic acid hybridization. Mixtures of such nucleic acid hybridization probes are also within the scope of this embodiment of the invention. Nucleic acid probes as provided herein are useful for detecting MSOR receptor gene expression in cells and tissues using techniques well-known in the art, including but not limited to Northern blot hybridization, in situ hybridization and Southern hybridization to reverse transcriptase-polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (PFLP) associated with certain genetic disorders The invention provides an isolated and purified, naturally-occurring, endogenous mammalian peptide ligand that specifically binds to the MSOR -receptor of the invention. For the purposes of this invention it will be understood that a ligand is any biologically active molecule that specifically binds to an MSOR opioid receptor of the -invention. The ligands of the invention include synthetic embodiments of the naturally-occurring peptide ligand isolated as described herein, as well as analogues, derivatives and variants of this peptide that specifically bind to the MSOR receptor. Such analogues include substitution variants, wherein an amino acid is substituted conservatively with another amino acid that does not ablate the specific binding properties of the peptide ligand. Specifically provided by the invention are substitution variants wherein the substituted amino acid is Leu$^{14}$, wherein this residue is substituted with tyrosine.

Each peptide ligand of the invention is comprised of a sequence of amino acids. The term amino acid as used in this invention is intended to include all $_L$- and $_D$-amino acids, naturally occurring and otherwise.

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$-$C_{16}$ ester, or converted to an amide of formula $NR_1R_2$ wherein R. and $R_2$ are each independently H or $C_1$-$C_{16}$ alkyl, or combined to form a heterocyclic ring, such as 5- or 6-membered. Amino groups of the peptide, whether amino-terminal or sidechain, may be in the form of a pharmaceutically-acceptable acid addition salt, such as the HCl, HBr, acetic, benzoic, E toluene sulfonic, maleic, tartaric and other organic salts, or may be modified to $C_1$-$C_{16}$ alkyl or dialkyl amino or further converted to an amide. Hydroxyl groups of the peptide sidechain may be converted to $C_1$-$C_{16}$ alkoxy or to a $C_1$-$C_{16}$ ester using well-recognized techniques. Phenyl and phenolic rings of the peptide sidechain may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide sidechains can be extended to homologous $C_1$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Peptidomimetic and organomimetic embodiments are also hereby explicitly declared to be within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial biological activity. For computer modelling applications, a pharmacophore is an idealized, three-dimensional definition of the structural requirements for biological activity. Peptido- and organomimetics can be designed to fit each pharmacophore with current computer modelling software (computer aided drug design). The degree of overlap between the specific activities of pharmacophores remains to be determined. It will be understood that mimetics prepared using such techniques that specifically bind to the MSOR receptor and developed using the peptide ligands of the invention will fall within the scope of the appended claims.

The peptides provided by the present invention can be chemically synthesized by any of a number of manual or automated methods of synthesis known in the art. Automated synthetic routines such as those available for use with automated peptide synthesizers are also intended to come within the scope of the present invention. Chemical derivatization, using the methods disclosed in this specification or other methods well known in the art, of naturally-occurring peptides or peptides purified from mixtures of protein degradation products, degraded by enzymatic or chemical means, are also within the scope of this invention, as are peptides made by molecular or genetic engineering means. Preferably, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/ hydroxybenzotriazole (HBTU/HOBT), and using p-hydroxymethylphenoxymethylpolystyrene (HMP) or Sasrin™ resin for carboxyl-terminus acids or Rink amide resin for carboxyl-terminus amides.

Fmoc-derivatized amino acids are prepared from the appropriate precursor amino acids by tritylation with triphenylmethanol in trifluoroacetic acid, followed by Fmoc derivitization as described by Atherton et al. (1989, *Solid Phase Peptide Synthesis*, IRL Press: Oxford).

Sasrin™ resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5–3 hours at room temperature.

Crude peptides are purified by preparative high pressure liquid chromatography (HPLC) using a Waters Delta-Pak C18 column and gradient elution with 0.1% TFA in water modified with acetonitrile. After column elution, acetonitrile is evaporated from the eluted fractions, which were then lyophilized. The identity of each product so produced and purified is confirmed by fast atom bombardment mass spectroscopy (FABMS) or electrospray mass spectroscopy (ESMS).

The production of proteins such as the opioid receptor proteins of the invention from cloned genes by genetic engineering means is well known in this art. The discussion which follows is accordingly intended as an overview of this field, and is not intended to reflect the full state of the art.

DNA encoding an opioid receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from the opioid receptor (MSOR) disclosed herein. Probes may be labeled with any detectable group and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an MSOR receptor as provided herein. See U.S. Pat. Nos. 4,683,195 to Mullis et al. and 4,683,202 to Mullis.

Opioid receptor protein may be synthesized in host cells transformed with a recombinant expression construct comprising a nucleic acid encoding the opioid receptor cDNA. For the purposes of this invention, a recombinant expression construct is a replicable DNA construct in which a nucleic acid encoding an opioid receptor is operably linked to suitable control sequences capable of effecting the expression of the opioid receptor in a suitable host. Generally, control sequences include a transcriptional promoter, an optional operator sequence to control transcription, a sequence encoding suitable mRNA ribosomal binding sites, and sequences which control the termination of transcription and translation. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). A preferred vector is RcRVS (Invitrogen, San Diego, Calif.).

Cultures of cells derived from multicellular organisms are a desirable host for recombinant opioid receptor protein synthesis. Transformed host cells are cells which have been transformed or transfected with recombinant expression constructs made using recombinant DNA techniques and comprising nucleic acid encoding an amino acid transporter protein. Transformed host cells may express the opioid receptor protein; when expressed, the opioid receptor of the invention will typically be located in the host cell membrane. See, Sambrook et al., ibid. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Ltk cell lines and WI138, BHK, COS-7, CV, and MDCK cell lines. CHO cells, COS-7 cells and Ltk⁻ cells are preferred.

The recombinant expression constructs of the present invention are useful to transform cells which do not ordinarily express an opioid receptor to thereafter express the receptor. Such cells are useful as intermediates for making cell membrane preparations useful for receptor binding activity assays, which are in turn useful for drug screening. The recombinant expression constructs of the present invention thus provide a method for obtaining reagents for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful psychoactive drugs synthesized, discovered or extracted from natural sources each year.

The recombinant expression constructs of the present invention are useful to detect, isolate, characterize and identify novel endogenous opioid receptor agonists and antagonists found in plasma, serum, lymph, cerebrospinal fluid, seminal fluid, or other potential sources of such compounds.

The utility of the present invention for using the nucleic acids of the invention to produce cell membranes containing the opioid receptor protein encoded thereby, and the demonstrated utility of this aspect of the invention to permit the isolation, characterization and identification of a novel peptide, termed orphanin FQ herein, as an endogenous receptor-binding ligand, enables rational drug design of novel therapeutically-active drugs using currently-available techniques (see Walters, "Computer-Assisted Modeling of Drugs", in Klegerman & Groves, eds., 1993, *Pharmaceutical Biotechnology*, Interpharm Press:Buffalo Grove, Ill., pp. 165–174).

The invention provides homogeneous compositions of a novel mammalian opioid receptor protein produced by transformed eukaryotic cells as provided herein. Each such homogeneous composition is intended to be comprised of the MSOR receptor protein that comprises at least 90% of the protein in such a homogenous composition. The invention also provides membrane preparations from cells expressing the MSOR receptor protein as the result of transformation with a recombinant expression construct, as described herein.

Mammalian opioid receptor proteins made from cloned genes in accordance with the present invention may be used for screening opioid analogues, or agonists or antagonists of opioid binding, or for determining the amount of such agonists or antagonists are present in a solution of interest (e.g., blood plasma, cerebrospinal fluid or serum). For example, host cells may be transformed with a recombinant expression construct of the present invention, a mammalian MSOR receptor expressed in those host cells, and the cells or membranes thereof used to screen compounds for their effect on opioid agonist binding activity. By selection of host cells that do not ordinarily express a MSOR receptor, pure preparations of membranes containing the transporter can be obtained.

The invention also provides ligands for such MSOR receptor proteins, including naturally-occurring ligands and synthetic embodiments thereof. Methods for identifying other, alternative ligands, and agonists and antagonists of peptide ligand binding are also provided by the invention. Such methods include competitive binding assays, wherein the peptide ligands of the invention are detectably labeled and incubated under competitive binding conditions with varying amounts of any putative ligand compound to be tested. The extent of inhibition of labeled ligand binding is useful in characterizing the extent and affinity of binding of novel ligands to the MSOR receptor. Specificity of binding can also be determined using such assays. Preferably, the peptide ligand of the invention being used in such competition experiments is detectably labeled with a radioisotope, such as I-123, I-125 and I-131.

The invention also provides antibodies that are immunologically reactive to the opioid receptor protein or epitopes thereof provided by the invention. The antibodies provided by the invention may be raised using methods well known in the art.

The present invention also provides monoclonal antibodies that are immunologically reactive with an epitope derived from an MSOR receptor of the invention, or fragment thereof. Such antibodies are made using methods and techniques well known to those of skill in the art. Monoclonal antibodies provided by the present invention are produced by hybridoma cell lines, that are also provided by the invention and that are made by methods well known in the art.

The ligands of the invention are useful as diagnostic and therapeutic agents when constituted as pharmaceutical compositions with the appropriate carriers or diluents. In diagnostic embodiments, detectably-labeled peptide ligands are used in methods for diagnosing diseases or pathological conditions related to ligand binding of MSOR receptors in vivo. Similarly, therapeutic methods of treatment are encompassed by the invention and provided using pharmaceutical compositions of such peptides administered in vivo in therapeutically-effective amounts.

Preparation of pharmaceutically acceptable compositions of the peptides of the present invention can be accomplished using methods well known to those with skill in the art. Any of the common carriers such as sterile saline solution, plasma, etc., can be utilized with the peptides provided by the invention. Routes of administration include but are not limited to oral, intravenous, parenteral, rectal, optical, aural and transdermal. Peptides of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

Embodiments of the invention comprising medicaments can be prepared for oral administration, for injection, or other parenteral methods and preferably include conventional pharmaceutically acceptable carriers, adjuvents and counterions as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 µg/kg to about 10 mg/kg of body weight are contemplated.

The invention also provides methods for detecting the amount of an analyte in a solution wherein the analyte is an endogenous peptide ligand of the invention in a biological sample, such as blood, serum, plasma or cerebrospinal fluid. In such methods is provided a first mixture comprised of cells or membranes heterologously expressing the MSOR opioid receptor of the invention, a second mixture comprised of a standard amount of a detectably-labeled embodiment of the peptide ligands of the invention, and a third mixture comprised of a diagnostically-significant tissue sample or bodily fluid. From these mixtures is produced a specific binding reaction mixture by contacting the first, second and third mixtures and incubating the reaction mixture for a time sufficient to allow binding between the peptide ligand and the MSOR receptor. The extent of the binding reaction is determined by calculating the amount of the detectably-labeled peptide ligand of the invention bound to the MSOR receptor, and comparing the amount of binding of the peptide ligand to the MSOR receptor in the presence of the tissue sample or bodily fluid of the third provided mixture with the amount of binding found in the absence of the tissue sample or bodily fluid of the third provided mixture.

The Examples which follow are illustrative of specific embodiments of the invention, and various uses thereof. They set forth for explanatory purposes only, and are not to be taken as limiting the invention.

EXAMPLE 1

Isolation of a Mammalian Opioid Receptor Probe by Random PCR Amplification of Rat Brain-derived cDNA Using Degenerate Oligonucleotide Primers In order to clone novel mammalian G-protein coupled receptors, cDNA prepared from RNA from different regions of mammalian (rat) brain was used as template for a polymerase chain reaction (PCR)-based random cloning experiment. PCR was performed using a pair of degenerate oligonucleotide primers derived from a mouse δ-opioid receptor (Kieffer et al., 1992, Proc. Natl. Acad. Sci. USA 89: 12048–12052; Evans et al., 1992, Science 258: 1952–1955). PCR products obtained in this experiment were characterized by nucleotide sequencing and used to isolate a full-length cDNA from a rat brain cDNA library.

The PCR amplification experiments were performed as described in co-owned and co-pending U.S. Ser. No. 08/149, 093, now U.S. Pat. No. 5,658,783, incorporated by reference, using the following primers: Primer III (sense):

ATGAATTCAC(G/A/C/T)(A/G)T(G/C)ATGAG(C/T)GT(G/C)GAC(C/A)G(C/A)TA (SEQ ID NO:1)

and
Primer VII (antisense):

TTGTCGAC(G/A)TA(G/A)AG(A/G)A(T/C)(G/A/C/T)GG(G/A)TT (SEQ ID NO:2).

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). A multiplicity of bacterial colonies comprising each of the subcloned fragments were used to make bacterial colony lifts on nitrocellulose filters using conventional techniques (see Sambrook, et al., ibid.). Such filters were hybridized with a [$^{32}$P]-dCTP-labeled radioactive nucleic acid probe comprising a full-length mouse δ-opioid receptor cDNA at a concentration of $1\times10^6$ cpm/mL under low stringency hybridization conditions [35% formamide, 5×standard citrate saline (SSC; wherein 1×SSC is 0.15M NaCl/0.015M sodium citrate, pH 7.0), 5× Denhardt's solution (wherein 1×Denhardt's solution is 0.02 g/mL each of bovine serum albumin, Ficoll and polyvinylpyrrolidone)] at 37° C. overnight. After hybridization, the filters were washed in a solution of 2×SSC/0.1% sodium dodecyl sulfate (SDS) at 55° C. and then exposed to X-ray film (XAR-5, Eastman-Kodak, Rochester, N.Y.) for 2 days at −70° C. using tungsten-impregnated intensifying screens (DuPont-NEN, Wilmington, Del.). Plasmid DNA from hybridizing clones was purified and the nucleotide sequence of the insert cDNA determined by the dideoxynucleotide chain termination method (Sanger et al., 1977, Proc. Natl. Acad. Sci. USA 74: 5463–5467) using Sequenase3 (U.S. Biochemical Corp., Cleveland, Ohio).

EXAMPLE 2

Isolation of a Novel Mammalian Opioid Receptor cDNA

One of the PCR products (termed LC132) were isolated and sequenced in this way and were fund to have a high degree of homology to the mouse δ-opioid receptor sequence (Evans et al., ibid. and Kieffer et al., ibid.). A full-length cDNA clone corresponding to this PCR fragment was isolated from a cDNA library prepared in the cloning vector λgt11 comprising oligo(dT)primed rat brain cDNA, as described in co-pending and co-pending U.S. Ser. No. 08/149,093 now U.S. Pat. No. 5,658,783.

Nucleotide sequence analysis performed essentially as described (see, Sambrook, ibid.) revealed the sequence shown in FIGS. 1A and 1B (SEQ ID No.:3). The putative protein product of the gene is also shown in FIGS. 1A and 1B (SEQ ID No:4). The sequence was found to have an open reading frame comprising 1101 nucleotides encoding a protein 367 amino acids in length-, and having a predicted molecular weight of 47 kilodaltons prior to post-translational modification. The sequence immediately 5' to the proposed initiation codon was found to contain several translation termination codons in-frame with the open reading frame, supporting the assignment of the translation start site. Predicted transmembrane domains [using the algorithm of Eisenberg et al. (1984, J. Molec. Biol. 179: 125–142)] are boxed and identified by Roman numerals (I–VII), and three sites of possible N-linked glycosylation are identified in the amino-terminal portion of the protein with solid triangles. Potential protein phosphorylation sites found in predicted cytoplasmic loops are marked with an asterisk. Further, a pair of cysteine residues conserved among known opioid receptors were found in the first and second predicted extracellular loops. On the basis of this analysis, this cloned nucleic acid was determined to be a novel mammalian opioid receptor. Comparison of the amino acid sequence of the novel receptor with the amino acid sequences of other known mammalian opioid receptors supported this conclusion.

The predicted amino acid sequences of this novel opioid receptor (SEQ ID No.:4), the rat μ-opioid receptor (SEQ ID No.:7, Chen et al., ibid.), the mouse δ-opioid receptor (at al, ibid and Kieffer et al., ibid.) and the mouse κ-Opioid receptor ((SEQ ID No.:9, Yasuda et al., ibid.) are aligned FIG. 2A and 2B. Overbares indicate predicted transmembrane regions I through VII in the protein product of the genes. Amino acid residues that are found in common between all four mammalian opioid receptors are presented in boldface.

Overall, the novel mammalian receptor disclosed herein had 47% overall identity with the other mammalian opioid receptors, which similarity rose to 67% when only the predicted transmembrane domains were considered. A more detailed comparison of these amino acid sequences are quantified in Table I, showing the percentage extent of homology in pairwise fashion between the different opioid receptors. Comparisons are made individually at each transmembrane domain (TMI-TMVII), as an average over all transmembrane domains (TMavg) and as the average degree of amino acid sequence homology for each protein as a whole (avg/all). In total, 145 of the 367 residues are shared with the other mammalian opioid receptors, confirming the conclusion that the novel mammalian receptor disclosed herein is an opioid receptor.

EXAMPLE 3

Construction of a Recombinant Expression Construct, DNA Transfection and Functional Expression of the Novel Mammalian Opioid Receptor In order to biochemically characterize the novel mammalian opioid receptor described in Example 2, and to confirm that it encodes a novel opioid receptor, the cDNA was cloned into a mammalian expression construct, the resulting recombinant expression construct transfected into COS-7 cells (for transient expression assays) and mouse Ltk⁻ cells (for stable expression assays), and cell membranes (COS-7) or cell lines (Ltk⁻) were generated that expressed the receptor protein in cellular membranes at the cell surface. Such cells and membranes isolated from such cells were used for biochemical characterization experiments as described in U.S. Ser. No. 0/8149,093, now U.S. Pat. No. 5,658,783.

The entire coding region of the receptor cDNA insert was subcloned in to the RcRSV vector (Invitrogen, San Diego, Calif.) using conventional techniques (see Sambrook et al., ibid.). Such recombinant expression constructs were introduced into COS-7 cells using the calcium-phosphate precipitation technique (Chen & Okayama, 1987, Molec. Cell. Biol. 7: 2745–2752), the transfected cells allowed to express the receptor for between 24–96 hours, and then cell membranes containing the receptor were isolated. The protein concentration was adjusted to 15–80 μg/sample for each of the binding studies described below.

These recombinant expression constructs were also introduced into Ltk⁻ cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Specific binding assays using a variety of opioid receptor agonists and antagonists were performed on membranes from both transient and stable transfectants. Ligand binding experiments were performed essentially as described in Bunzow et al. (1988, Nature 336: 783–787, and U.S. Ser. No. 08/149,093, now U.S. Pat. No. 5,658,783). In binding experiments, increasing amounts of membrane protein (from 15–80 μg) was incubated with the radioactively-labeled opioid agonist or antagonist to be tested for 120 min at 22° C. in a total volume of 1 ml. However, in these experiments no specific binding was found for the following compounds (their known receptor binding specificities are noted in parentheses): [$^3$H]-Tyr-$_D$Ala-Gly-Met-Phe-Gly-ol (DAMGO; μ-opioid receptor agonist), [$^3$H]-c[$_D$-penicillamine$^2$, $_D$penicillamine$^5$]enkephalin (DPDPE; δ agonist), [$^3$H]-U-69,593 (κ agonist), [$^3$H]-diprenorphine (μ agonist), [$^3$H]-bremacozine (κ agonist), [$^3$H]-dihydromorphine (μagonist), [$^3$H]-ethylketocyclazocine (κ agonist) or [$^{125}$I]-β-endorphin. Although low levels of specific binding were seen using [$^3$H]-naloxone (μantagonist), the significance of these results was compromised by the fact that untransfected COS-7 and Ltk⁻ cells also shown endogenous low levels of specific [$^3$H]-naloxone binding.

Figure 4A:
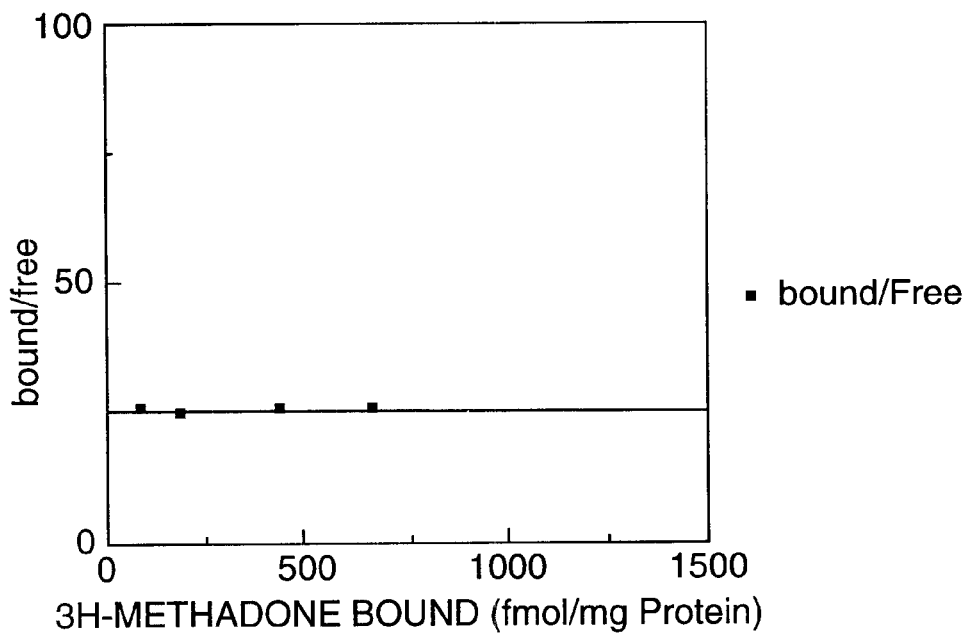
FIGS. 4A and 4B presents affinity binding experiment results of $^3$H-methadone binding to COS-7 cells (FIG. 4A) and to COS-7 cells expressing the novel mammalian MSOR opioid receptor of the invention
Figure 4B:
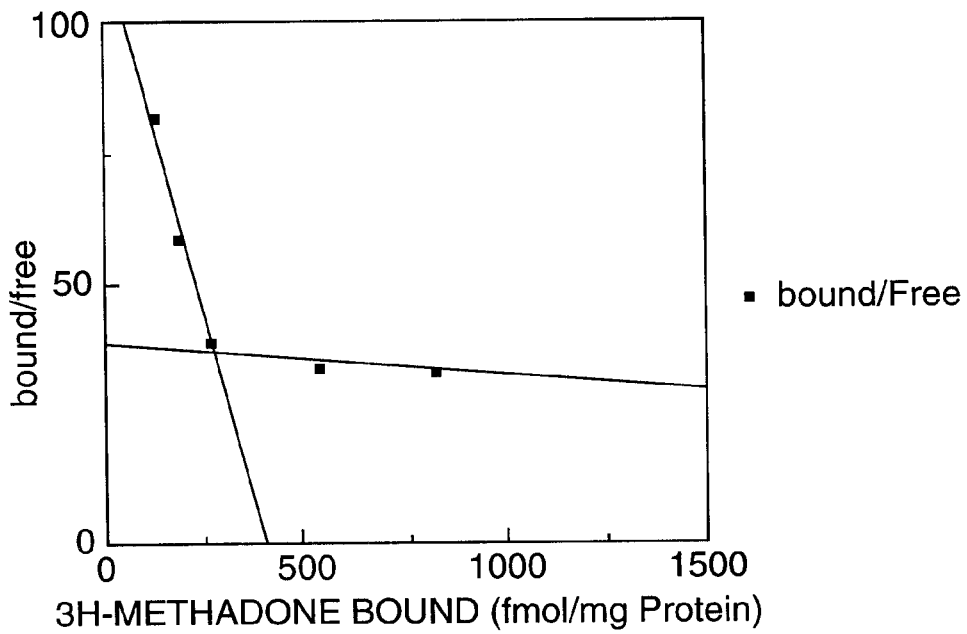

Surprisingly, however, specific binding was found using [$^3$H]-methadone. The results of Scatchard analysis of the methadone binding data are shown in FIGS. 4A and 4B.

For Scatchard analysis experiments, 0.25 ml aliquots of crude plasma membrane homogenate from transfected cell cultures was incubated in duplicate with increasing concentrations of [$^3$H]methadone (70.3 Ci/mmol; 10–3000 pM final concentration) under conditions described above. The estimated value for $B_{max}$ was derived from these data were obtained using the LIGAND computer program. FIG. 4A shows the results of radiolabeled methadone binding with untransfected COS-7 cells; similar results were found with Ltk⁻ cell membranes. These results demonstrate no or negligible amounts of endogenous methadone binding by these cell membranes. FIG. 4B shows the results using COS-7 cells transfected with the RcRSV-LC132 expression construct. The levels of specific binding shown in this graph correspond-to a dissociation constant ($K_D$) of about $10^{-10}$ M for methadone and a $B_{max}$ of about400–450 femtomoles/μg protein for the novel mammalian opioid receptor expressed by these cells.

Thus, the novel mammalian opioid receptor disclosed herein has the heretofore unknown property of exhibiting specific binding to the opiate analog, methadone, while. showing no specific.-binding to a variety of other known opioid receptor agonists and antagonists. These results support the conclusion that the receptor disclosed herein is a completely novel and heretofore unsuspected member of the opioid receptor family, termed herein therefore MSOR.

EXAMPLE 4

Brain Tissue Distribution of MSOR Opioid Receptor Expression

The distribution of mRNA corresponding to expression of the MSOR receptor gene in various regions of the rat brain was determined by in situ hybridization of rat brain slices, as described in U.S. Ser. No. 08/149,093, now U.S. Pat. No. 5,568,783.

Results of these experiments are shown in FIG. 3, Panel A shows a section through the frontal cortex, preoptic area and caudate putamen; Panel B shows a section through the hypothalamus, thalamus and hippocampus; and Panel C shows a section through the pons and cerebellum. These experiments localized high level MSOR expression in the hypothalamus (arcuate (Arc), posterior (PH), lateral (LH) and ventromedial (VMH) hypothalamic nuclei, Panel B), certain nuclei of the thalamus (paraventricular thalamic nuclei (PVP), Panel B), the medial habenula (MHb, Panel B), the CA regions of the hypothalamus, the dentate gyrus (DG, Panel B), the locus coeruleus and certain cortical areas (medial preoptic are (MPA), Panel A and the cortex (Cx), Panel B). Virtually no signal was seen in the caudate putamen (Cpu, Panel A) or cerebellum (Cb, Panel C). Strong hybridization was also detected in sections of the brainstem (Panel C) and the spinal cord (not shown).

These results demonstrate that the MSOR receptor disclosed herein is expressed in rat brain in a variety of anatomically-distinct sites, suggesting an important role for this receptor in both higher brain function and central nervous system control of motor and sensory nerve signalling.

EXAMPLE 5

Identification of an Endogenously occurring Peptide Ligand for the MSOR Opioid Receptor Due to the high level of sequence homology between the MSOR opioid receptor and the $\mu$-, $\delta$- and $\kappa$-opioid receptors found as disclosed in Example 2, it was appreciated that the novel receptor disclosed herein might specifically recognize an endogenous peptide ligand, and respond to binding such a ligand using a second messenger signalling system similar to those found associated with the previously-described opioid receptors. Since the MSOR opioid receptor had been found to be expressed in cells in the central nervous system in Example 4, and since MSOR opioid receptor mRNA is highly expressed in hypothalamus, porcine hypothalamic homogenates were screened for receptor binding activity. Inhibition of forskolin-stimulated, cyclic adenosine monophosphate (cAMP) accumulation in cells heterologously expressing the MSOR opioid receptor was used as an assay, which assay had been used to characterize the interaction of other opioid receptors and their ligands.

Acetic acid extracts of porcine hypothalamic tissues were prepared as follows. 4.5 kg of freshly frozen porcine hypothalamic tissue were extracted in 9L of a solution of 0.5M acetic acid/10 mM ascorbic acid/1 mM EDTA. The extract was centrifuged to remove insoluble debris and the supernatant absorbed batchwise onto a C_silica matrix. Unbound material was removed by washing with water, and specifically-bound material was then eluted in a solution of 80% methanol. A total of 2L of methanolic eluate were then concentrated by rotary evaporation to a final volume of 44 mL, and material having a molecular weight less than 10 kilodaltons was obtained by ultrafiltration using an Amicon Centriprep 10 column (Amicon, Beverly, Mass.). This material was applied in ten separate experiments to a cation exchange HPLC column (ProteinPak SP 8HR, 10×100 mm, Waters) equilibrated with 10 mM $NH_4COO$. The column was developed with a linear gradient of $NH_4COO$ in 10% methanol at a flow rate of 1 mL/min; a total of 80 1 mL fractions were collected. 10% (100 $\mu$L) of each of 5 consecutive fractions were pooled and lyophilized, resulting in 16 pools. 5% of each pool was tested in duplicate for the capacity to inhibit forskolin-stimulated cAMP accumulation in cells heterologously expressing the MSOR opioid receptor.

Assays of ligand binding-associated inhibition of forskolin-stimulated cAMP accumulation in cells heterologously expressing the MSOR receptor were performed as follows. CHO cells, deficient in dihydrofolate reductase (dhfr⁻) were transfected with MSOR opioid receptor-encoding cDNA cloned into the expression vector pRcRSV (Invitrogen), as described in Example 3 above, using calcium phosphate co-precipitation (Okayama and Chen, ibid.). Stably-transfected clones were selected using G418, and screened for MSOR expression using a reverse transcriptase-PCR protocol (RT-PCR; Rappolee et al., 1988; *Science* 241: 1823–1825). One clone that tested positively for MSOR expression (LC-7) was used in ligand binding experiments.

For determination of cAMP levels, receptor-transfected CHO cells (i.e., LC-7) or untransfected CHO/dhfr⁻ cells, were plated in 24-well culture plates and grown to confluency. After removal of culture media, aliquots of HPLC fractions prepared as described above in a total volume of 0.2 mL DMEM containing 10 mM HEPES buffer, pH 7.4, 1 mM forskolin and 1 mM Ro 20–1724 (Rolipram, RBI) were added per well and cells incubated at 37° C. for 10 min. Cellular reactions were halted by the addition of 0.5 mL ice-cold ethanol, and plates were stored for 12 h or overnight at 80° C. Frozen plates were centrifuged and aliquots of the supernatant were removed and dried onto 96-well plates for cAMP determinations. cAMP determinations were performed using a commercially-available kit (Biotrak SPA, Amersham) essentially according to the manufacturer's instructions.

Figure 5:
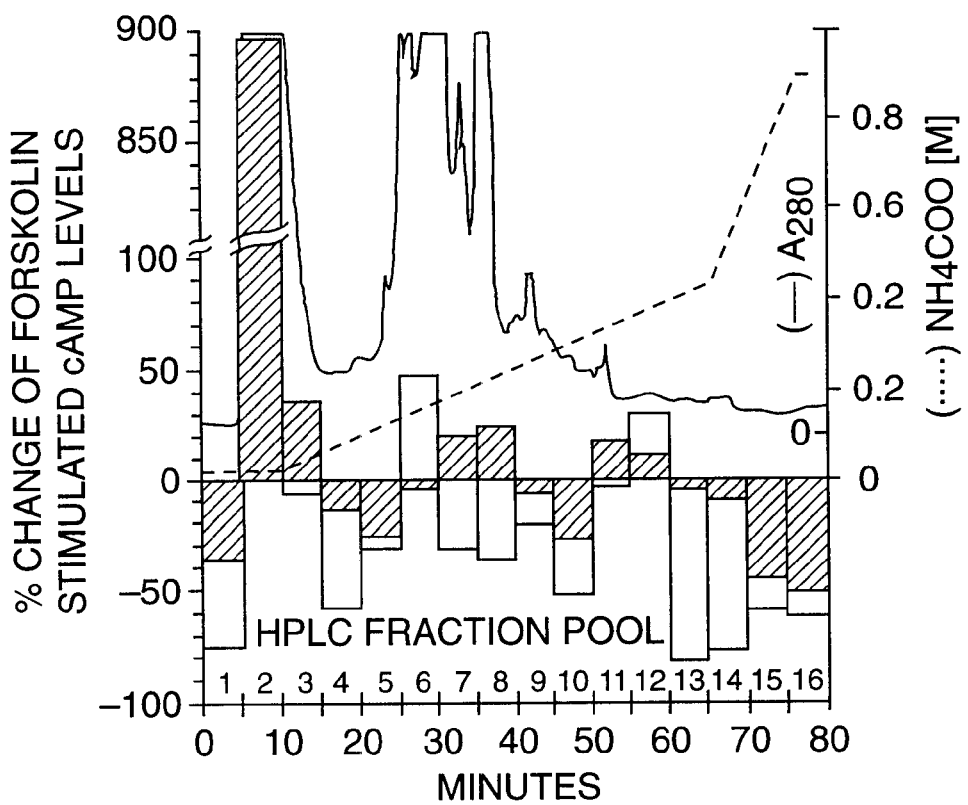
FIG. 5 shows the extent of inhibition of forskolin-stimulated cAMP accumulation in CHO cell heterologously expressing the MSOR of the invention by fractions of acetic acid-extracted peptides from porcine hypothalamus, wherein $A_{280}$ represents absorbance at 280 nm, shaded bars represent results obtained with untransfected CHO cells and open bars represent results obtained with MSOR transfected CHO cells.

The results of these experiments are shown in FIG. 5. Open bars represent results obtained with MSOR-expressing transfected CHO cells, and shaded bars represent results obtained with untransfected CHO cells. Pools 13 and 14 (corresponding to fractions 61–70 consistently showed adenyl cyclase inhibitory activity in transfected versus untransfected cells. The large increase in cAMP detected in fraction 2 is due to endogenous cAMP extracted from the tissue. Fractions 60–67 were found to contain most of the detected bioactivity, and were pooled for further purification by reverse-phase HPLC.

Figure 6:
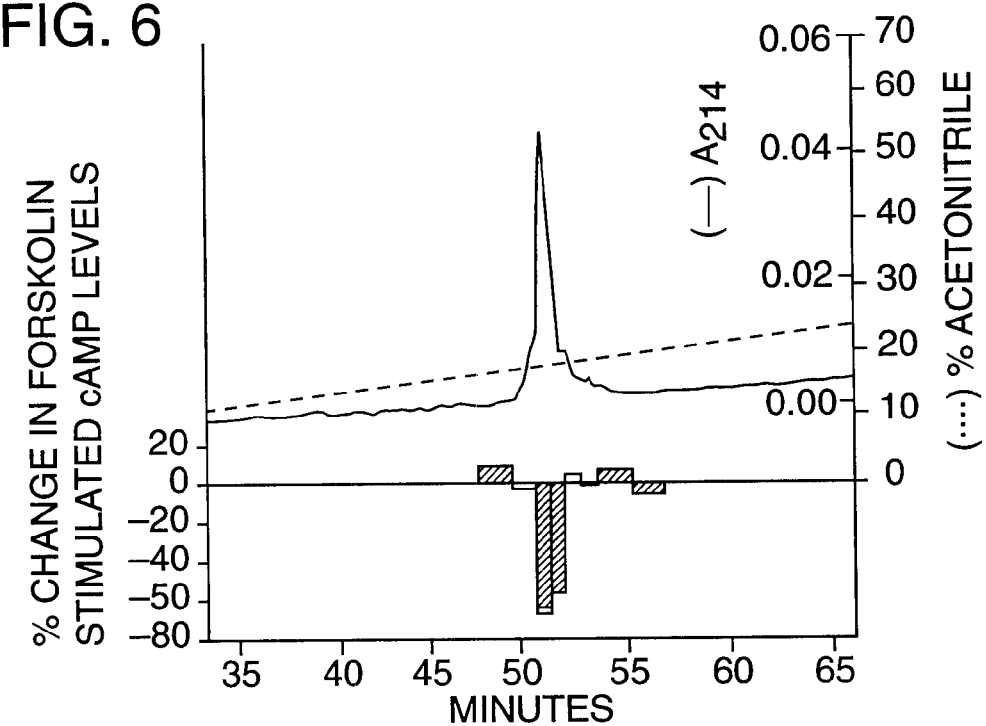
FIG. 6 shows the extent of inhibition of forskolin-stimulated cAMP accumulation in CHO cell heterologously expressing the MSOR of the invention by fractions of reverse-phase HPLC fractionated acetic acid-extracted peptides from porcine hypothalamus, wherein $A_{214}$ represents absorbance at 214 nm, and shaded bars represent results obtained with MSOR transfected CHO cells.

Reverse-phase HPLC was performed on pooled fractions 60–67 as follows. The complete bioactive material was loaded onto an octyl silica column (Superspher RP Select B, 2×125 mm, Merck) and eluted at a flow rate of 0.12 mL/min with a linear gradient of acetonitrile in 0.1% trifluoroacetic acid (TFA). Aliquots of fractions from this gradient were tested as described above, and the results of these assays shown in FIG. 6. Inhibition of forskolin-stimulated cAMP in MSOR-transfected CHO cells (shaded bars) was detected only in the major peak of eluted protein (measured as absorbance at 214 nm ($A_{214}$)).

The isolated material having adenyl cyclase inhibitory activity was analyzed by mass spectrometry and sequenced by Edman degradation. The material was determined to be a peptide having the sequence:

Phe-Gly-Gly-Phe-Thr-Gly-Ala-Arg-Lys-Ser-Ala-Arg-Lys-Lu-Ala-Asn-Gln (SEQ ID No.:5).

(Abbreviations for amino acids can be found in Zubay, *Biochemistry* 2d ed., 1988, MacMillan Publishing: New York, p. 33). Final yields of this peptide were about 200 picomoles from 4.5 kg hypothalamic tissue (wet weight). A computer database search revealed that this peptide had not been reported, either as a unique entity or as part of a larger protein. This peptide is designated orphanin FQ herein.

The primary structure of this novel peptide was compared with the primary structure of a number of other, naturally-occurring opioid peptides, as shown, in FIG. 7. The amino terminal tetrapeptide sequence motif YGGF (amino acids 1–4 of SEQ ID No.:13) of the known opioid receptor ligands is strictly similar to the amino terminal sequence FGGF (SEQ ID No.:14) found in orphanin FQ (SEQ ID No.:5). Further, two clusters of basic amino acids found in the orphanin FQ (SEQ ID No.:5) peptide dee the arrangement of positively-charged residues in Dynorphin A (SEQ ID No.:6) and Endorphin (SEQ ID No.:11). However, none of these peptides could be shown to bind to the MSOR opioid receptor, suggesting a structural/functional divergence of the orphanin FQ peptide from these other opioid receptor ligands.

In order to verify that the isolated material had the observed properties of the pooled fraction from which it was isolated, a synthetic peptide having the deduced sequence was made and was found to be identical to the isolated peptide in its elution profile in reverse-phase HPLC. assay and in molecular weight as determined by mass spectrometry. Moreover, the synthetic peptide was also found to inhibit adenyl cyclase production in forskolin-stimulated CHO cells transfected with and heterologously expressing the MSOR opioid receptor (??), having an $EC_{50}$ of 1.58 nM (±0.66 nM) and showing maximal inhibition (80%) at a concentration of about 100 nM. This high potency is comparable to that of other neuropeptides identified as the naturally-occurring ligands of other CNS-specific receptors. Thus, the isolated sequence, termed orphanin FQ herein, represents a novel endogenous peptide ligand for the MSOR opioid receptor.

To further characterize ligand binding of this novel ligand to the MSOR receptor, a series of peptide analogues were prepared that were tyrosine-substituted at different positions in the peptide sequence. cAMP inhibitions assays were performed using both the tyrosine-substituted peptides and monoiodotyrosine substituted peptides. Iodinated peptide was synthesized using the chloramine T method of Hunter and Greenwood (1962, *Nature* 194: 495). From these studies it was determined that the peptide analog having tyrosine at position 14 (Y-14; SEQ ID No.:6) and its monoiodo form (I-Y14) were MSOR agonists of almost equivalent potency to the orphanin FQ peptide, having $EC_{50}$ values of 1 nM and 3 nM, respectively.

Figure 8:
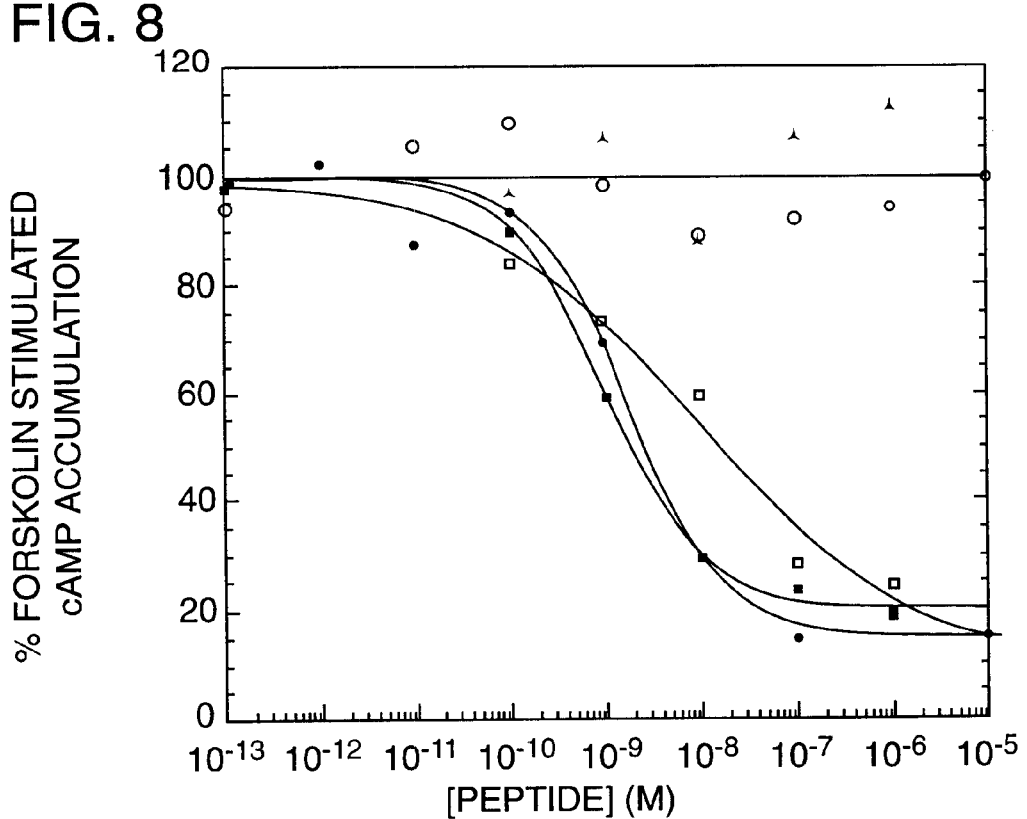
FIG. 8 is a graph illustrating the extent of inhibition of forskolin-stimulated cAMP accumulation in MSOR transfected CHO cells by the peptides orphanin FQ (filled circles, SEQ ID No.:5); Y14-orphanin FQ (filled squares, SEQ ID No.:6) monoiodinated Y14-orphanin FQ (open squares) and Leu-Enkephalin (open circles, SEQ ID No.:13). Orphanin FQ-treated untransfected CHO cells are shown as filled triangles.

FIG. 8 shows a comparison of adenyl cyclase inhibitory activity of orphanin FQ (filled circles), Y14 orphanin FQ (filled squares), monoiodo Y14 orphanin FQ (open squares) and Leu-Enkephalin (open circles) in transfected CHO cells heterologously expressing the MSOR receptor; untransfected CHO cells were treated with orphanin FQ peptide as a control (filled triangles). Data were normalized so that cAMP levels in forskolin-stimulated, untransfected CHO cells was equal to 100%. cAMP levels were determined with all incubations being done at least twice in triplicate. FIG. 8 shows the results of a representative experiment.

The Y14 peptide was used to quantitatively assay receptor binding affinity for the novel ligand. Membranes from MSOR transfected CHO cells (LC-7) were used at a concentration of 55 μg membrane protein/assay. Membranes were incubated with increasing concentrations of (125I)-Y14-orphanin FQ in a final volume of 0.2 mL binding buffer (50 mM HEPES, pH 7.4, 10 mM NaCl, 1 mM MgCl2, 2.5 mM CaCl2, 0.1% bovine serum albumin, 0.025% bacitracin) containing 1mg wheat germ agglutinin-coated SPA beads (Amersham). Iodinated peptide was synthesized as above using the chloramine T method. The monoiodinated species was obtained as a single peak, having a specific activity of 2200 Ci/mmole on the day of synthesis. Assays were performed in 96-well plates (OptiPlate, Caberra Packard), and the mixtures were incubated with shaking for 1 h. Bound ligand-associated radioactivity were determined by scintillation proximity (see, for example, Nelson, 1987, *Anal. Biochem.* 165: 287; Bosworth and Towers, 1989, *Nature* 341: 167) using a TopCount microplate scintillation counter (Canberra Packard). Concentrations of free ligand were calculated by subtracting the amount of specifically-bound ligand from the total amount of radioligand added.

Figure 9:
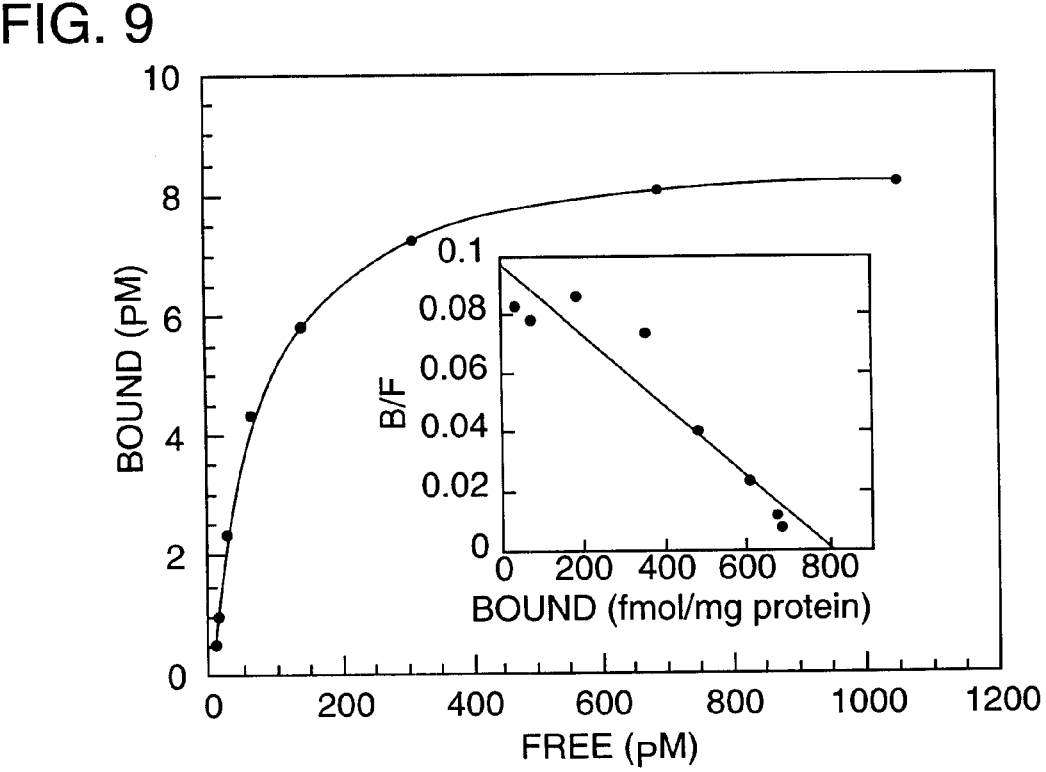
FIG. 9 is a graph of ($^{251}$I)-labeled Y14-orphanin FQ binding to isolated membranes from MSOR transfected CHO cells. The inset is a Scatchard analysis of these results.

The results of these experiments are shown in FIG. 9. The radiolabeled monoiodo-Y14-orphanin FQ peptide displayed saturable and displaceable binding to membranes of MSOR-expressing transfected cells, having a $K_d$ of 0.3 nM and a $B_{max}$ of 77.8 fmol/mg membrane protein. These experiments demonstrate that the novel. endogenous ligand peptide, orphanin FQ, and Y14-tyrosine substituted analogues thereof, bind saturably to the MSOR opioid receptor with high affinity, further confirming the conclusion that this peptide is a naturally-occurring, endogenous ligand for this receptor. These experiments also indicate that the Y14substituted peptide can be used as a radioligand to detect and quantify MSOR opioid receptor levels.

EXAMPLE 6

Functional Characterization of the Orphanin FQ Peptide

In order to study the physiological activity of the orphanin FQ peptide, the in vivo activity of the peptide was investigated on unrestricted animals, and specifically, on nociception in such animals.

Figure 10A:
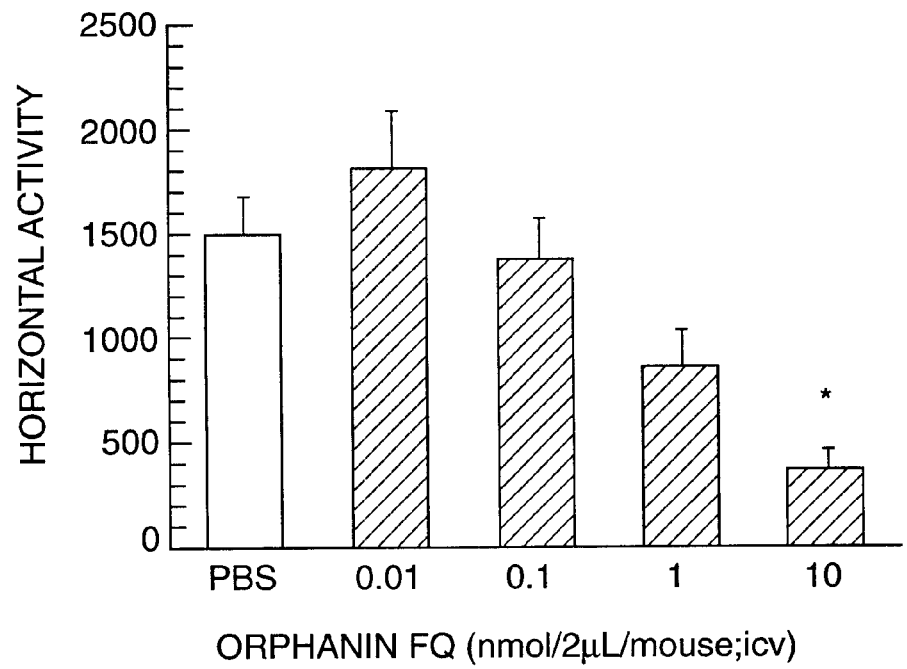
FIGS. 10A and 10B show the effects on horizontal activity (FIG. 10A) and vertical activity (FIG. 10B) in mice treated with varying concentrations of orphanin FQ peptide.
Figure 10B:
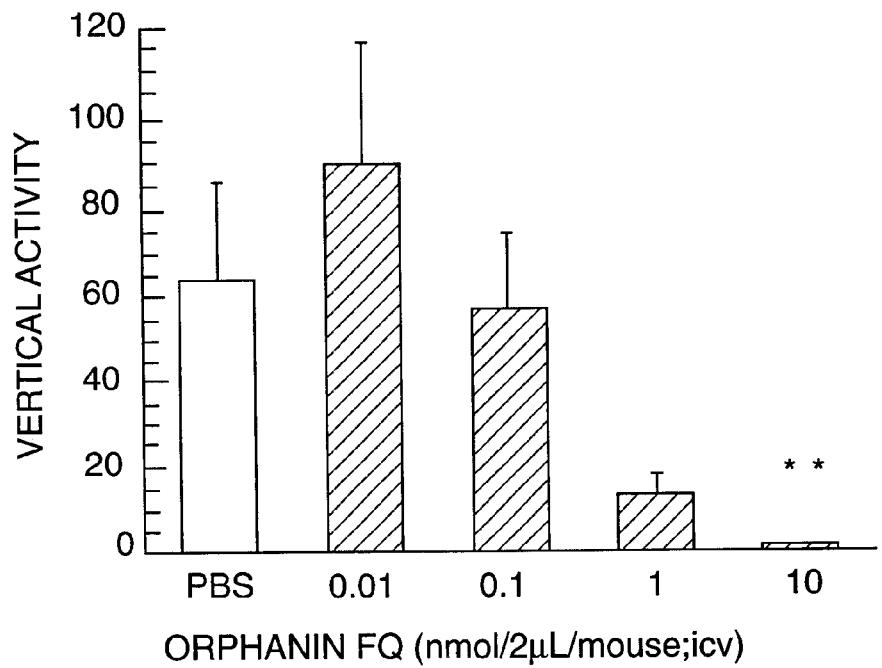

For these experiments, the peptide was administered intracerebroventricularly (i.c.v.) and intrathecally (i.t.) in mice. Immediately after peptide administration, mice were placed in transparent boxes in groups of three and behavioral signs recorded. Emphasis was placed on signs indicative of depressant, stimulant and autonomic effects of the peptide (as described by Irwin, 1968, *Psychopharmacologia* 13: 222). In open-field observation experiments, the peptide was noted to have a profound influence on locomotor activity, as well as a decrease in muscle tone, a loss of righting reflex, and ataxia. A quantitative investigation showed a decrease of both horizontal and vertical locomotion following i.c.v. administration of the peptide at concentrations of 0.1–10 nmol/2 μL/mouse. These results are shown in FIGS. 10A and 10B. The effects of the peptide on horizontal (FIG. 10A) and vertical (FIG. 10B) locomotor activity was measured using Digiscan Animal Activity Monitors (Omnitech, Columbus Ohio). The values for horizontal and vertical locomotor activity represent the total number of interruptions of the horizontal and vertical sensors during the first 10 min following administration of the peptide. Data are shown as the mean ± standard error of the mean.

Figure 11:
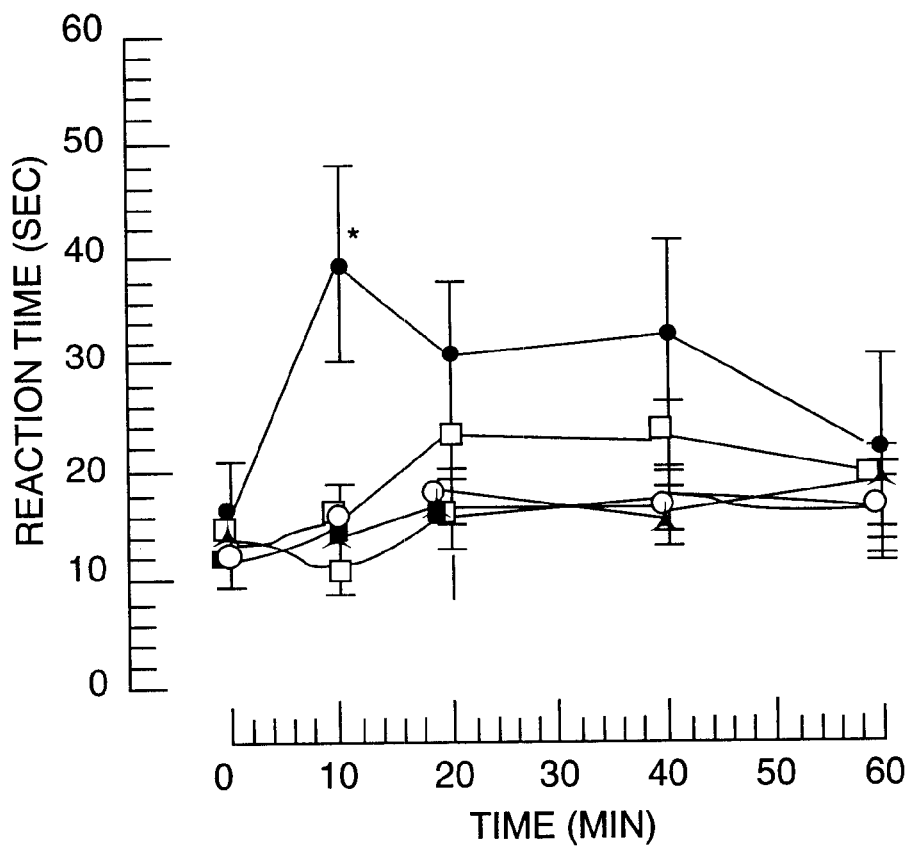
FIG. 11 illustrates the effects of orphanin FQ peptide on nociception in mice as determined using a hotplate assay.
Figure 12:
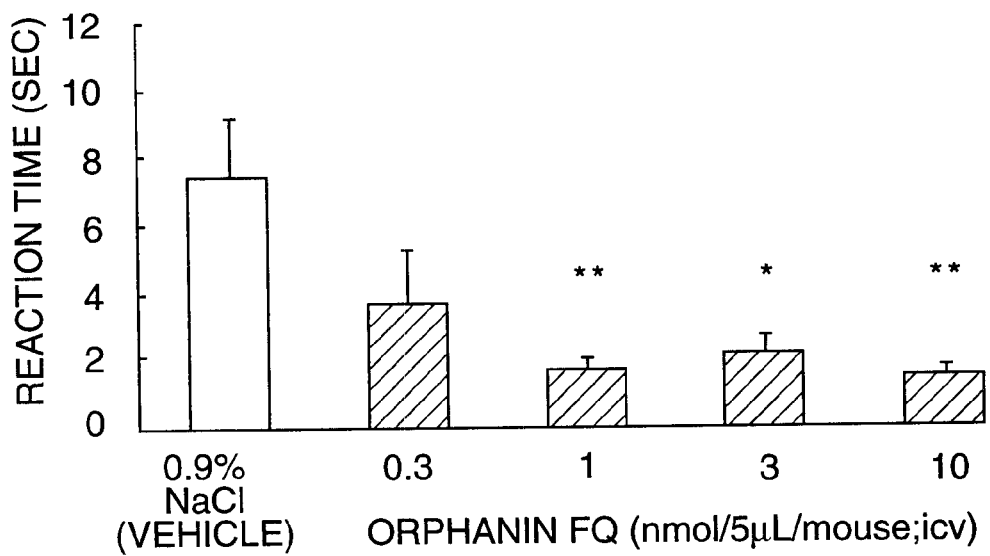
FIG. 12 shows the effects of orphanin FQ peptide on nociception in mice as determined using a tail-flick assay.

On the other hand, the orphanin FQ peptide showed little analgesic effect in these mice, as recorded in a hot plate test, as shown in FIG. 11. Groups of 6–8 male MORO mice (weight=22 g) were administered phosphate buffered saline (open circles) or varying doses of the orphanin peptide. Reaction time represents the time taken for the mice to lick their paws. The hot plate was set to 58° C., and a cutoff time of 60 sec was used. No significant inhibition of nociception was detected, with the exception of mice administered the highest levels of peptide, 10 nmol/mouse, i.c.v. (designated by an asterisk). This observation was most likely related to a decrease in locomotor activity and muscle tone. At all doses tested, all animals exhibited normal toe- and tail-pinch reflexes, as shown in FIG. 12. No analgesic effect was observed when orphanin FQ was administered i.t. at 2.5–10 nmol/4 µL/animal; however, at the highest dose, hindlimb paralysis and decrease in locomotor activity was observed. No analgesic effect was observed in any mouse with this peptide at doses that did not produce significant decreases in motor activity and muscle tone. These results indicate that, despite structural homology with analgesia-producing opioid receptor ligands as described in Example 5, the orphanin FQ peptide appears to be pharmacologically distinct and to lack appreciable analgesic activity.

It should be understood that the foregoing disclosure emphasizes certain specific embodiments of the invention and that all modifications or alternatives equivalent thereto are within the spirit and scope of the invention as set forth in the appended claims.

TABLE I

|  | TMI | TMII | TMIII | TMIV | TMV | TMVI | TMVII | TM avg | avg/all |
|---|---|---|---|---|---|---|---|---|---|
| LC132[a] vs rat µ[a] | 58[b] | 67 | 77 | 48 | 67 | 59 | 85 | 66 | 48 |
| LC132 vs rat κ[c] | 35 | 67 | 82 | 43 | 71 | 73 | 80 | 64 | 47 |
| LC132 vs mouse δ[d] | 46 | 67 | 77 | 52 | 63 | 59 | 75 | 63 | 46 |
| rat κ vs mouse δ | 62 | 83 | 91 | 57 | 75 | 64 | 90 | 75 | 52 |
| rat µ vs mouse δ | 69 | 90 | 86 | 48 | 83 | 77 | 85 | 77 | 51 |
| rat µ vs rat κ | 54 | 80 | 91 | 33 | 75 | 73 | 95 | 72 | 49 |

[a]Bunzow et al.
[b]percent
[c]Minami et al. (1993) FEBS Letters 329, 291.
[d]Evans et al. (1992) Science 258, 1952.

What we claim is:

1. A method of screening a test compound for a capacity to competitively bind to a mammalian methadone-specific opioid receptor (MSOR) in cells expressing the MSOR, the method comprising:

(a) transforming a host cell with an expression vector comprising a nucleic acid encoding the MSOR;

(b) culturing the transformed host cell under conditions that would allow expression of the MSOR;

(c) assaying the transformed cell culture for binding of an amount of a detectably-labeled peptide, wherein the peptide has a sequence comprising: Xaa-Gly-Gly-Phe-$(A^1)$-$(A^2)$-$(A^3)$-$(A^4)$-$(A^5)$-$(A^6)$-$(A^7)$-$(A^8)$-$(A^9)$-$(A^{10})$-$(A^{11})$-$(A^{12})$-Gln wherein Xaa is Phe or Tyr; $A^1$ is Tbr, Leu or Met; $A^2$ is Gly, Arg or Thr; $A^3$ is Ala, Arg or Ser; $A^4$ is Arg, Ile, Glu or Gln; $A^5$ is Lys, Arg, or Phe; $A^6$ is Ser, Pro or Lys; $A^7$ is Ala, Lys, Gln or Val; $A^8$ is Arg, Leu, Thr or Val; $A^9$ is Lys, Pro or Thr; $A^{10}$ is Tyr, Leu or Trp; $A^{11}$ is Ala, Asp or Val; $A^{12}$ is Asn or Thr; (SEQ ID NO:15), wherein at least one amino acid at position $A^1$ to $A^{12}$ is uniquely found in a corresponding position of SEQ ID NO:5 or 6; and wherein amino acids are each individually in either the D or L stereochemical configuration and wherein the peptide specifically binds to a mammalian MSOR in competition with varying amounts of the test compound; and (d) determining whether the test compound competitively binds to the MSOR by calculating an extent of inhibition of binding of the detectably-labeled peptide in the presence of the test compound.

2. The method of claim 1 further comprising comparing an extent of inhibition of binding of the test compound with an extent of inhibition of binding of additional compounds that are known to competitively bind to mammalian opioid receptors, wherein said additional compounds comprise naturally-occurring and synthetic opioid receptor agonists and antagonists.

3. The method of claim 1, wherein the detectably-labeled peptide has the amino acid sequence shown in SEQ ID NO:5 or 6 or a sequence shown in SEQ ID NO:5 or 6 which contains one or more conservative amino acid substitutions but still binds to the mammalian MSOR.

4. The method of claim 3, wherein the detectably-labeled peptide has an amino acid sequence shown in SEQ ID NO:5 or 6.

5. The method of claim 1, wherein the detectably-labeled peptide inhibits adenyl cyclase production in forskolin-stimulated CHO cells transfected with and expressing the MSOR wherein said peptide has an $EC_{50}$ of about 1–3 nM.

6. A method of screening a test compound for a capacity to competitively bind to a mammalian MSOR in cells expressing the MSOR, the method comprising:

(a) transforming a host cell with an expression vector comprising the nucleic acid encoding MSOR having the amino acid sequence as set forth in SEQ ID NO:4;

(b) culturing the transformed host cell under conditions that would allow expression of MSOR;

(c) assaying the transformed cell culture for binding of an amount of a detectably-labeled peptide having the formula set forth in SEQ ID NO:5 or 6 and wherein the peptide specifically binds to a mammalian opioid receptor having an amino acid sequence identified by SEQ ID NO:4 in competition with varying amounts of the test compound; and (d) determining whether the test compound competitively binds to the opioid receptor by calculating an extent of inhibition of binding of the detectably-labeled peptide in the presence of the test compound.

7. The method of claim 6 further comprising comparing an extent of inhibition of binding of the test compound with an extent of inhibition of binding of additional compounds that are known to competitively bind to mammalian opioid receptors, wherein said additional compounds comprise naturally-occurring synthetic opioid receptor agonists and antagonists.

8. The method of claim 1 wherein transforming the host cell comprises transforming the host cell with an expression vector encoding the MSOR having an amino acid sequence of SEQ ID NO:4.

9. The method of claim 3, wherein the amino acid sequence shown in SEQ ID NO:5 or 6 contains only one conservative amino acid substitution.

10. A method of screening a test compound for a capacity to competitively bind to a mammalian MSOR in cells expressing the MSOR, the method comprising:

(a) transforming a host cell with an expression vector comprising a nucleic acid encoding the MSOR having the amino acid sequence as set forth in SEQ ID NO:4;

(b) culturing the transformed host cell under conditions that would allow expression of the MSOR;

(c) assaying the transformed cell culture for binding of an amount of a detectably-labeled peptide, wherein the peptide has an amino acid sequence shown in SEQ ID NO:5 or 6; and wherein amino acids are each individually in either the D or L stereochemical configuration and wherein the peptide specifically binds to a mammalian MSOR having an amino acid sequence identified by SEQ ID NO:4 in competition with varying amounts of the test compound; and (d) determining whether the test compound competitively binds to the MSOR by calculating an extent of inhibition of binding of the detectably-labeled peptide in the presence of the test compound.

11. The method of claim 1, wherein $A^4$ is Arg.

12. The method of claim 1, wherein $A^8$ is Arg.

* * * * *

UNITED STATES PATENT AND TRADEMARK OFFICE
CERTIFICATE OF CORRECTION

PATENT NO. : 6,406,866 B1
DATED : June 18, 2002
INVENTOR(S) : Grandy et al.

It is certified that error appears in the above-identified patent and that said Letters Patent is hereby corrected as shown below:

Title page,
Item [56], References Cited, OTHER PUBLICATIONS, under "*Cunningham*" (first line), "HgH" should read -- High --.
Under "*Cunningham*" (second line), "High" should read -- HgH --.
Under "*Cunningham*" (third line), "Source" should read -- Science --.

Column 1,
Line 6, "is a is a" should read -- is a --.

Column 2,
Line 4, "Scd." should read -- Sci. --.
Line 60, "avia" should read -- via --.

Column 4,
Line 35, "1-125" should read -- I-125 --.

Column 7,
Line 49, "($^{251}$I)" should read -- ($^{125}$I) --.
Line 63, "."novel" should read -- "novel --.

Column 8,
Line 11, "depicted FIGS." should read -- depicted in FIGS. --.
Line 35, "(PFLP)" should read -- (RFLP) --.
Line 56, "R." should read -- $R_1$ --.
Line 61, "E toluene" should read -- toluene --.

Column 9,
Line 5, "$C_1$" should read -- $C_2$ --.

Column 14,
Line 11, "5xstandard" should read -- 5X standard --.
Line 11, "1xSSC" should read -- 1X SSC --.
Line 12, "5x Denhardt's" should read -- 5X Denhardt's --.
Line 13, "1XDenhardt's" should read -- 1X Denhardt's --.
Line 25, "Sequenase3" should read -- Sequenase® --.
Line 38, "oligo(dT)primed" should read -- oligo(dT)-primed --.
Line 39, "the first "co-pending" should read -- co-owned --.
Line 48, "length-," should read -- length, --.

UNITED STATES PATENT AND TRADEMARK OFFICE
CERTIFICATE OF CORRECTION

PATENT NO. : 6,406,866 B1  
DATED : June 18, 2002  
INVENTOR(S) : Grandy et al.

It is certified that error appears in the above-identified patent and that said Letters Patent is hereby corrected as shown below:

Column 15,  
Line 3, "(at al," should read -- (SEQ ID NO.:8; Evans *et al.*, --.  
Line 4, "κ-Opioid" should read -- κ-opioid --.  
Line 5, "((SEQ" should read -- (SEQ --.  
Line 6, "FIG. 2A" should read -- in FIGS. 2A --.  
Line 6, "overbares" should read -- overbars --.  
Line 44, "0/8149,093" should read -- 08/149,093 --.

Column 16,  
Line 18, "µagonist" should read -- µ agonist --.  
Line 20, "µantagonist" should read -- µ antagoinst --.  
Line 41, "correspond-to" should read -- correspond to --.  
Line 47, "while." should read -- while --.  
Line 48, "specific.-binding" should read -- specific binding --.

Column 17,  
Line 23, "Endogenously occurring" should read -- Endogenously-occurring --.  
Line 47, "C.silica" should read -- $C_{18}$silica --.

Column 19,  
Line 7, "dee" should read -- resemble --.  
Line 8, "No.:6" should read -- No.:10 --.  
Line 9, "Endorphin" should read -- α-Endorphin --.  
Line 18, "HPLC." should read -- HPLC --.

Column 23,  
Line 5, "t tgctcagtc" should read -- ttgctcagtc --.  
Line 6, "g cgcccagct" should read -- gcgcccagct --.  
Line 7, "a gggtgacag" should read -- agggtgacag --.  
Line 11, "g ag" should read -- gag --.  
Line 12, "G lu" should read -- Glu --.  
Line 14, "c tg" should read -- ctg --.  
Line 15, "L eu" should read -- Leu --.  
Line 17, "t gc" should read -- tgc --.  
Line 18, "C ys" should read -- Cys --.  
Line 20, "a gg" should read -- agg --.  
Line 21, "A rg" should read -- Arg --.  
Line 23, "g ca" should read -- gca --.  
Line 24, "A la" should read -- Ala --.  
Line 26, "g ac" should read -- gac --.

UNITED STATES PATENT AND TRADEMARK OFFICE
CERTIFICATE OF CORRECTION

PATENT NO. : 6,406,866 B1
DATED : June 18, 2002
INVENTOR(S) : Grandy et al.

Page 3 of 6

It is certified that error appears in the above-identified patent and that said Letters Patent is hereby corrected as shown below:

Column 23 cont'd,
Line 27, "A sp" should read -- Asp --.
Line 29, "g tc" should read -- gtc --.
Line 30, "V al" should read -- Val --.
Line 32, "a cc" should read -- acc --.
Line 33, "T hr" should read -- Thr --.
Line 35, "g cc" should read -- gcc --.
Line 36, "A la" should read -- Ala --.
Line 38, "a ta" should read -- ata --.
Line 39, "I le" should read -- Ile --.
Line 41, "t ca" should read -- tca --.
Line 42, "S er" should read -- Ser --.
Line 44, "g cc" should read -- gcc --.
Line 45, "A la" should read -- Ala --.
Line 47, "t tt" should read -- ttt --.
Line 48, "P he" should read -- Phe --.
Line 50, "a tg" should read -- atg --.
Line 51, "M et" should read -- Met --.
Line 53, "a ag" should read -- aag --.
Line 54, "L ys" should read -- Lys --.
Line 56, "g ct" should read -- gct --.
Line 57, "A la" should read -- Ala --.

Column 25,
Line 2, "c aa" should read -- caa --.
Line 3, "G ln" should read -- Gln --.
Line 5, "c gc" should read -- cgc --.
Line 6, "A rg" should read -- Arg --.
Line 8, "c tc" should read -- ctc --.
Line 9, "L eu" should read -- Leu --.
Line 11, "t gc" should read -- tgc --.
Line 12, "C ys" should read -- Cys --.
Line 14, "c gg" should read -- cgg --.
Line 15, "A rg" should read -- Arg --.
Line 17, "g ta" should read -- gta --.
Line 18, "V al" should read -- Val --.
Line 20, "c tacacccaa" should read -- ctacacccaa --.

UNITED STATES PATENT AND TRADEMARK OFFICE
CERTIFICATE OF CORRECTION

PATENT NO. : 6,406,866 B1
DATED : June 18, 2002
INVENTOR(S) : Grandy et al.

It is certified that error appears in the above-identified patent and that said Letters Patent is hereby corrected as shown below:

Column 25 cont'd,
Line 21, "c atctggagc" should read -- catctggagc --.
Lines 28 and 30, "G lu" should read -- Glu --.
Line 32, "L eu" should read -- Leu --.
Line 34, "C ys" should read -- Cys --.
Line 36, "A rg" should read -- Arg --.
Lines 38, 46 and 52, "A la" should read -- Ala --.
Line 40, "A sp" should read -- Asp --.
Line 42, "V al" should read -- Val --.
Line 44, "T hr" should read -- Thr --.
Line 48, "I le" should read -- Ile --.
Line 50, "S er" should read -- Ser --.
Line 54, "P he" should read -- Phe --.

Column 27,
Line 2, "M et" should read -- Met --.
Line 4, "L ys" should read -- Lys --.
Line 6, "A la" should read -- Ala --.
Lines 8 and 52, "G ln" should read -- Gln --.
Line 10, "A rg" should read -- Arg --.
Line 12, "L eu" should read -- Leu --.
Lines 14 and 50, "C ys" should read -- Cys --.
Line 16, "A rg" should sread -- Arg --.
Line 18, "V al" should read -- Val --.
Lines 27 and 38, "A la" should read -- Ala --.
Line 46, "S er" should read -- Ser --.

Column 29,
Lines 2 and 4, "T yr" should read -- Tyr --.
Lines 6 and 12, "I le" should read -- Ile --.
Line 8, "P he" should read -- Phe --.
Lines 10 and 20, "L eu" should read -- Leu --.
Line 14, "H is" should read -- His --.
Line 16, "V al" should read -- Val --.
Line 18, "M et" should read -- Met --.
Lines 22 and 24, "C ys" should read -- Cys --.
Line 26, "G ly" should read -- Gly --.
Line 28, "L eu" should read -- Leu --.
Line 30, "T yr" should read -- Tyr --.

UNITED STATES PATENT AND TRADEMARK OFFICE
CERTIFICATE OF CORRECTION

PATENT NO. : 6,406,866 B1
DATED : June 18, 2002
INVENTOR(S) : Grandy et al.

It is certified that error appears in the above-identified patent and that said Letters Patent is hereby corrected as shown below:

Column 29 cont'd,
Lines 32, 36 and 40, "T hr" should read -- Thr --.
Lines 34 and 49, "L eu" should read -- Leu --.
Line 38, "S er" should read -- Ser --.
Lines 42 and 53, "A la" should read -- Ala --.
Line 51, "P he" should read -- Phe --.

Column 31,
Lines 2 and 4, "V al" should read -- Val --.
Lines 6 and 12, "L eu" should read -- Leu --.
Lines 8 and 10, "A la" should read -- Ala --.
Lines 14 and 26, "L ys" should read -- Lys --.
Line 16, "C ys" should read -- Cys --.
Line 18, "A la" should read -- Ala --.
Line 20, "P ro" should read -- Pro --.
Lines 22 and 24, "L eu" should read -- Leu --.
Lines 28 and 30, "V al" should read -- Val --.
Line 32, "A la" should read -- Ala --.
Line 34, "P ro" should read -- Pro --.
Line 36, "G ln" should read -- Gln --.
Line 38, "A rg" should read -- Arg --.
Lines 40 and 51, "S er" should read -- Ser --.
Line 49, "A sp" should read -- Asp --.
Line 53, "G ly" should read -- Gly --.

Column 33,
Lines 3 and 17, "P ro" should read -- Pro --.
Line 5, "V al" should read -- Val --.
Line 7, "L ys" should read -- Lys --.
Line 9, "L eu" should read -- Leu --.
Lines 11 and 19, "S er" should read -- Ser --.
Line 13, "T yr" should read -- Tyr --.
Line 15, "A rg" should read -- Arg --.
Line 21, "A sp" should read -- Asp --.
Line 23, "T rp" should read -- Trp --.
Lines 25 and 31, "I le" should read -- Ile --.
Lines 27 and 29, "L eu" should read -- Leu --.
Line 33, "S er" should read -- Ser --.

UNITED STATES PATENT AND TRADEMARK OFFICE
CERTIFICATE OF CORRECTION

PATENT NO. : 6,406,866 B1
DATED : June 18, 2002
INVENTOR(S) : Grandy et al.

It is certified that error appears in the above-identified patent and that said Letters Patent is hereby corrected as shown below:

<u>Column 33 cont'd,</u>
Line 35, "A la" should read -- Ala --.
Line 37, "L eu" should read -- Leu --.
Line 39, "L ys" should read -- Lys --.
Line 41, "G ln" should read -- Gln --.
Line 53, "L ys" should read -- Lys --.

<u>Column 35,</u>
Line 11, "G ln" should read -- Gln --.
Line 21, "V al" should read -- Val --.
Line 48, "opioi d" should read -- opioid --.

<u>Column 37,</u>
Line 13, "G ln" should read -- Gln --.
Line 16, "Th r" should read -- Thr --.
Line 31, "ac id" should read -- acid --.
Line 35, "X aa" should read -- Xaa --.
Line 51, "Tbr," should read -- Thr, --.

Signed and Sealed this

Eighth Day of April, 2003

JAMES E. ROGAN
*Director of the United States Patent and Trademark Office*